(12) United States Patent
Stahl et al.

(10) Patent No.: US 11,147,987 B2
(45) Date of Patent: Oct. 19, 2021

(54) SYSTEM AND METHOD FOR COUCH SAG COMPENSATION IN IMAGE GUIDED RADIO THERAPY

(71) Applicant: SHANGHAI UNITED IMAGING HEALTHCARE CO., LTD., Shanghai (CN)

(72) Inventors: Johannes Stahl, Houston, TX (US); Supratik Bose, Houston, TX (US); Jonathan Maltz, Houston, TX (US); Lu Xu, Shanghai (CN); Hao Chen, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 9 days.

(21) Appl. No.: 16/832,110

(22) Filed: Mar. 27, 2020

(65) Prior Publication Data

US 2020/0222723 A1 Jul. 16, 2020

Related U.S. Application Data

(63) Continuation of application No. 16/219,364, filed on Dec. 13, 2018, now Pat. No. 10,610,702, which is a
(Continued)

(51) Int. Cl.
*A61N 5/10* (2006.01)
*A61B 6/03* (2006.01)
(Continued)

(52) U.S. Cl.
CPC ............ *A61N 5/1049* (2013.01); *A61B 6/032* (2013.01); *A61B 6/5276* (2013.01); *A61B 6/563* (2013.01);
(Continued)

(58) Field of Classification Search
CPC ...................... A61B 6/5276; A61N 2005/1057
See application file for complete search history.

(56) References Cited

U.S. PATENT DOCUMENTS 5,160,337 A * 11/1992 Cosman ................. A61B 6/102
378/17
5,872,829 A 2/1999 Wischmann et al.
(Continued)

FOREIGN PATENT DOCUMENTS

CN 102232835 A 11/2011
DE 202005014582 U1 2/2007

OTHER PUBLICATIONS

International Search Report in PCT/CN2017/086337 dated Jan. 26, 2018, 4 pages.
(Continued)

*Primary Examiner* — Gandhi Thirugnanam
(74) *Attorney, Agent, or Firm* — Metis IP LLC

(57) ABSTRACT

A method and system for using in a two-modality apparatus. The two-modality apparatus comprises a couch with a table top, a first modality unit and a second modality unit. A second image of a target portion of an object when the table top is at a second working position of the second modality unit may be acquired. A second sag of the table top at a second measurement point of the table top according to the second image may be determined based on the image. A difference between a first sag of the table top at a first measurement point of the table top and the second sag may be estimated based on the second sag and standard data. The standard data provides a relationship relating to a sag of the table top positioned between the first modality unit and second modality unit.

20 Claims, 20 Drawing Sheets

Related U.S. Application Data continuation of application No. 15/661,023, filed on Jul. 27, 2017, now Pat. No. 10,166,407, which is a continuation of application No. PCT/CN2017/086337, filed on May 27, 2017.

(51) Int. Cl.
- *A61B 6/00* (2006.01)
- *A47C 31/12* (2006.01)

(52) U.S. Cl.
CPC ......... *A61N 5/1039* (2013.01); *A61N 5/1069* (2013.01); *A47C 31/12* (2013.01); *A61B 6/566* (2013.01); *A61N 2005/1057* (2013.01); *A61N 2005/1061* (2013.01); *A61N 2005/1074* (2013.01)

(56) References Cited

U.S. PATENT DOCUMENTS

| | | | |
|---|---|---|---|
| 6,011,828 A | 1/2000 | Hardy et al. | |
| 6,333,971 B2* | 12/2001 | McCrory | A61K 49/0409 378/162 |
| 6,895,105 B2 | 5/2005 | Wollenweber | |
| 7,020,315 B2* | 3/2006 | Vaisburd | A61B 6/04 378/4 |
| 7,344,306 B2* | 3/2008 | Hsieh | A61B 6/032 378/20 |
| 7,607,833 B2 | 10/2009 | Marzendorfer | |
| 8,086,010 B2 | 12/2011 | Nabatame et al. | |
| 8,107,730 B2* | 1/2012 | Kariv | A61B 6/5276 382/182 |
| 8,511,894 B2* | 8/2013 | Gagnon | G06T 11/005 378/205 |
| 8,983,161 B2 | 3/2015 | Berkus et al. | |
| 10,166,407 B2* | 1/2019 | Stahl | A61N 5/1049 |
| 2002/0186819 A1 | 12/2002 | Proksa | |
| 2004/0015176 A1* | 1/2004 | Cosman | A61B 90/39 606/131 |
| 2007/0003020 A1* | 1/2007 | Hsieh | A61B 6/037 378/207 |
| 2007/0197908 A1* | 8/2007 | Ruchala | A61B 6/0487 600/427 |
| 2007/0297660 A1* | 12/2007 | Hsieh | A61B 6/583 382/131 |
| 2008/0031414 A1* | 2/2008 | Coppens | A61B 6/0492 378/65 |
| 2009/0022383 A1* | 1/2009 | Falco | A61B 6/583 382/131 |
| 2009/0080603 A1* | 3/2009 | Shukla | A61N 5/1049 378/25 |
| 2010/0027763 A1 | 2/2010 | Carlsson | |
| 2011/0200178 A1* | 8/2011 | Mansfield | A61N 5/10 378/209 |
| 2012/0189102 A1 | 7/2012 | Maurer, Jr. et al. | |
| 2014/0016759 A1* | 1/2014 | Ngar | A61B 6/583 378/207 |
| 2015/0204989 A1* | 7/2015 | Ni | G01N 23/046 378/62 |
| 2015/0213633 A1* | 7/2015 | Chang | A61N 5/1049 382/284 |
| 2016/0023019 A1* | 1/2016 | Filiberti | A61N 5/10 600/1 |
| 2016/0051429 A1 | 2/2016 | Yanagihara et al. | |
| 2017/0164931 A1 | 6/2017 | Ng et al. | |
| 2018/0110487 A1* | 4/2018 | Liu | A61N 5/1069 |
| 2018/0144510 A1* | 5/2018 | Lachaine | G06T 7/0012 |
| 2018/0339172 A1* | 11/2018 | Stahl | A61B 6/5276 |
| 2019/0126071 A1* | 5/2019 | Stahl | A61B 6/032 |
| 2019/0175122 A1* | 6/2019 | Stahl | A61B 6/0492 |
| 2020/0346042 A1* | 11/2020 | Maltz | G06T 11/005 |
| 2021/0090291 A1* | 3/2021 | Stahl | A61B 6/547 |

OTHER PUBLICATIONS

Written Opinion in PCT/CN2017/086337 dated Jan. 26, 2018, 4 pages.

Zhang, Shuhui et al., Quantity Control Discussion in Tumor Radiotherapy Positioning Technology, Chinese Journal of Medical Physics, 2013, 4 pages.

Hans L. Riis et al., Elekta Precise Table Characteristics of IGRT Remote Table Positioning, Acta Oncologica, 48(2):267-270, 2009.

\* cited by examiner

SYSTEM AND METHOD FOR COUCH SAG COMPENSATION IN IMAGE GUIDED RADIO THERAPY

CROSS-REFERENCE TO RELATED APPLICATIONS

This present application is a continuation of U.S. application Ser. No. 16/219,364, filed on Dec. 13, 2018, which is a continuation of U.S. application Ser. No. 15/661,023, filed on Jul. 27, 2017, which is a continuation of International Application No. PCT/CN2017/086337, filed on May 27, 2017, designating the United States of America, the contents of which are hereby incorporated by reference.

TECHNICAL FIELD

The present disclosure generally relates to image guided radio therapy (IGRT), and more particularly, to a system and method for couch sag compensation in IGRT.

BACKGROUND

IGRT is a widely used medical technique. For instance, an IGRT apparatus may include a CT imaging device and an RT device that share a same couch for supporting an object during an examination. However, compared to the couch of a conventional CT, the radiotherapy couch needs to extend longer from its support position into the bore of the CT gantry. As a result, the couch may sag or deflect along the longitudinal direction. The deflection of the couch from a horizontal baseline may be a function of both the weight of the object and the amount by which the couch extends along the longitudinal direction of the couch. Thus, it may be desirable to develop a method or a system to compensate the sag of a couch that may remove or reduce the error of object position to improve the quality of a radio therapy.

SUMMARY

The present disclosure relates to IGRT. One aspect of the present disclosure relates to a method for using in a two-modality apparatus, wherein the two-modality apparatus comprises a couch with a table top, a first modality unit having a first isocenter, and a second modality unit having a second isocenter. The method may include one or more of the following operations. The two-modality apparatus may be cased to position, based on a first characteristic point in a first image. The table top carrying an object at a first working position of the first modality unit may correspond to a first sag of the table top at a first measurement point of the table top. The first measurement point of the table top may relate to the first isocenter of the first modality unit. The first image may include a section representing a target portion of an object. A part of the target portion may correspond to the first characteristic point. A second image of the target portion of the object may be acquired when the table top is at a second working position of the second modality unit. A second sag of the table top at a second measurement point of the table top may be determined according to the second image. The second measurement point of the table top may relate to the second isocenter of the second modality unit. Standard data that provide a relationship relating to a sag of the table top positioned between the first modality unit and second modality unit may be retrieved. A difference between the first sag and the second sag may be estimated based on the second sag and the standard data. A second characteristic point in the second image may be determined based on the estimated difference of the first sag and the second sag. A registration may be performed between the first image and the second image based on the first characteristic point and the second characteristic point. The two-modality apparatus may move the table top to a vicinity of the first working position of the first modality unit based on the registration such that the target portion of the object aligns with the first isocenter of the first modality unit.

In some embodiments, the first standard parameter or the second standard parameter may be in the form of a table.

In some embodiments, the first standard parameter or the second standard parameter may relate to a weight of an object carried by the table top.

In some embodiments, the estimating a difference between the first sag and the second sag may comprise one or more of the following operations. A weight of the object may be obtained. The first sag of the table top may be determined based on the obtained weight of the object, a first amount of extension of the table top at a working position of the first modality unit, and the first standard parameter.

In some embodiments, the acquiring the second image of the target portion of the object when the table top is at the second working position of the second modality unit may comprise one or more of the following operations. The table top may be moved to the second working position of the second modality unit.

In some embodiments, the first image may be a planning image of the target portion of the object, the planning image may provide a treatment center of the first modality unit, the moving the table top to the vicinity of the first working position of the first modality unit may comprise one or more of the following operations. The first image and the second image may be compared after the registration. An adjustment of the treatment center of the first modality unit may be determined based on the comparison.

In some embodiments, the performing a registration between the first image and the second image may comprise one or more of the following operations. The first characteristic point with the second characteristic point may be aligned.

In some embodiments, the first modality unit may be a Linear Accelerator (LINAC) device.

In some embodiments, the second modality unit may be a computed tomography (CT) device.

In some embodiments, the CT device and the LINAC device may be arranged such that an imaging plane of the CT device may be perpendicular to a longitudinal axis passing through the first isocenter of the LINAC device and the second isocenter of the CT device.

Another aspect of the present disclosure relates a system for determining a couch sag in a two-modality apparatus, wherein the two-modality apparatus comprises a couch with a table top, a first modality unit having a first isocenter, and a second modality unit having a second isocenter. The system may include an image acquisition module, the image acquisition module may be configured to provide a planning image including a first characteristic point and a section representing a target portion of an object, a part of the target portion corresponding to the first characteristic point. The system may include a control module, the control module may be configured to cause the two-modality apparatus to position the table top carrying the object at a first working position of the first modality unit corresponding to a first sag of the table top at a first measurement point of the table top based on the first characteristic point in the planning image, the first measurement point of the table top relating to the first isocenter of the first modality unit. In some embodiments, the image acquisition module may further be configured to acquire a treatment image of the target portion of the object when the table top is at a second working position of the second modality unit. The system may include a parameter determination module, the parameter determination module may be configured to determine a second sag of the table top at a second measurement point according to the treatment image, the second measurement point of the table top relating to a second isocenter of the second modality unit. In some embodiments, the parameter determination module may further be retrieve standard data that provide a relationship relating to a couch sag of the table top. The system may include an image registration module, the image registration module may be configured to estimate, based on the second sag and the standard data, a difference of the second sag and the first sag. In some embodiments, the parameter determination module may further be configured to determine a second characteristic point in the treatment image based on the estimated difference of the second sag and the first sag. In some embodiments, the image registration module may further be configured to perform, based on the first characteristic point and the second characteristic point, a registration between the planning image and the treatment image. In some embodiments, the control module may further be configured to cause the two-modality apparatus to move the table top to a vicinity of the first working position of the modality unit based on the registration such that the target portion of the object aligns with the first isocenter of the first modality unit.

A further aspect of the present disclosure relates to a system. The system may comprise a two-modality apparatus, wherein the two-modality apparatus comprises a couch with a table top, a first modality unit having a first isocenter, and a second modality unit having a second isocenter. The system may further comprise at least one processor, and instructions that, when executed by the at least one processor, cause the system to effectuate a method. The at least one processor may provide a planning image including a first characteristic point and a section representing a target portion of an object, a part of the target portion corresponding to the first characteristic point. The at least one processor may cause the two-modality apparatus to position, based on the first characteristic point in the planning image, the table top carrying the object at a first working position of the first modality unit corresponding to a first sag at a first measurement point of the table top, the first measurement point of the table top relating to the first isocenter of the first modality unit. The at least one processor may obtain a treatment image of the target portion of the object when the table top is at a second working position of the second modality unit. The at least one processor may determine a second sag of the table top at a second measurement point according to the treatment image, the second measurement point of the table top relating to the second isocenter of the second modality unit. The at least one processor may retrieve standard data that provide a relationship relating to a sag of the table top. The at least one processor may estimate, based on the second sag and the standard data, a difference of the second sag and the first sag. The at least one processor may determine a second characteristic point in the treatment image based on the estimated difference of the second sag and the first sag. The at least one processor may perform a registration between the planning image and the treatment image based on the first characteristic point and the second characteristic point. The at least one processor may cause the two-modality apparatus to move the table top to a vicinity of the first working position of the first modality unit based on the registration such that the target portion of the object aligns with the first isocenter of the first modality unit.

A further aspect of the present disclosure relates to a non-transitory computer readable medium including executable instructions. The instructions, when executed by at least one processor, may cause the at least one processor to effectuate a method for determining a couch sag in a two-modality apparatus, wherein the two-modality apparatus comprises a couch with a table top, a first modality unit having a first isocenter, and a second modality unit having a second isocenter. In some embodiments, the non-transitory computer readable medium may include instructions for causing a computer to implement the method described herein.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid obscuring aspects of the present disclosure unnecessarily. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they may achieve the same purpose.

Figure 2A:
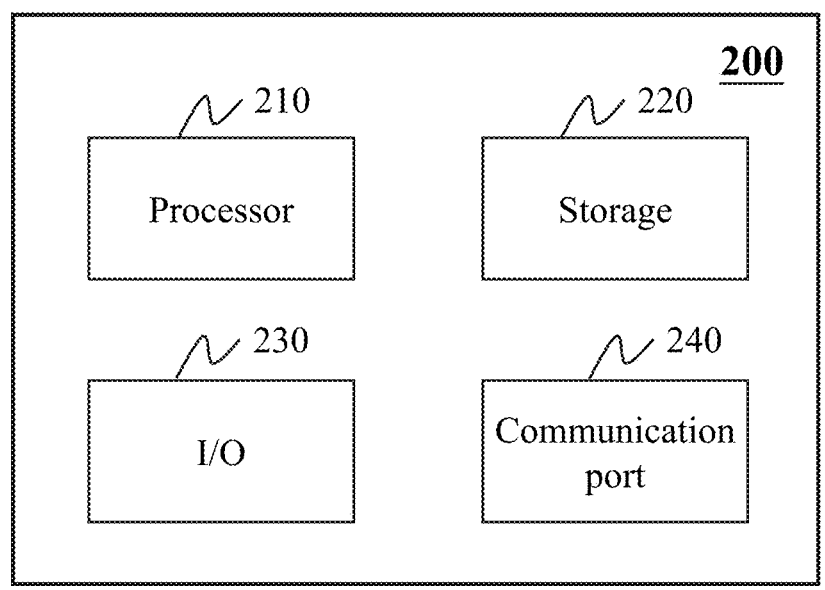
FIG. 2A is a schematic diagram illustrating exemplary hardware and/or software components of an exemplary computing device on which the processing engine may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2A) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The present disclosure relates to image guided radio therapy (IGRT). Specially, the present disclosure relates to a couch sag compensation system and method in IGRT. According to some embodiments of the present disclosure, the method may include obtaining a treatment CT image of an object at a CT position. The method may further include determining a sagging of a couch supporting the object during the CT scan based on the treatment CT image. The method may further include determining the sagging of the couch at an RT position based on the sagging of the couch during the CT scan, alone or in combination with standard data relating to, for example, a longitudinal position of a measurement point and a loaded weight.

The following description is provided to help better understanding of CT image reconstruction methods and/or systems. The term "image" used in this disclosure may refer to a 2D image, a 3D image, a 4D image, and/or any related image data (e.g., CT data, projection data corresponding to the CT data). This is not intended to limit the scope the present disclosure. For persons having ordinary skills in the art, a certain amount of variations, changes, and/or modifications may be deducted under the guidance of the present disclosure. Those variations, changes, and/or modifications do not depart from the scope of the present disclosure.

Figure 1A:
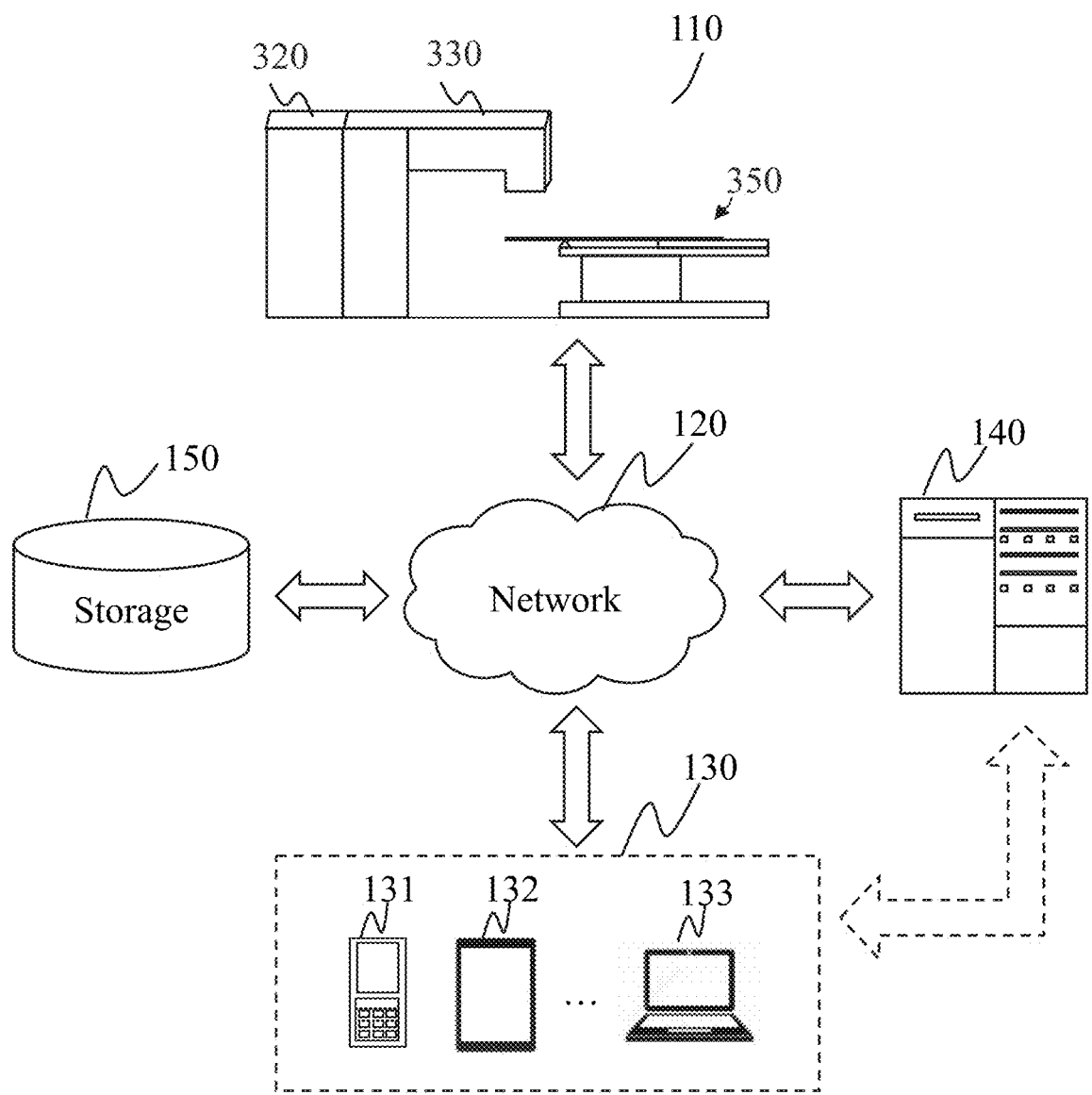
FIG. 1A and FIG. 1B illustrate a schematic diagram of a diagnostic and treatment system according to some embodiments of the present disclosure.
Figure 1B:
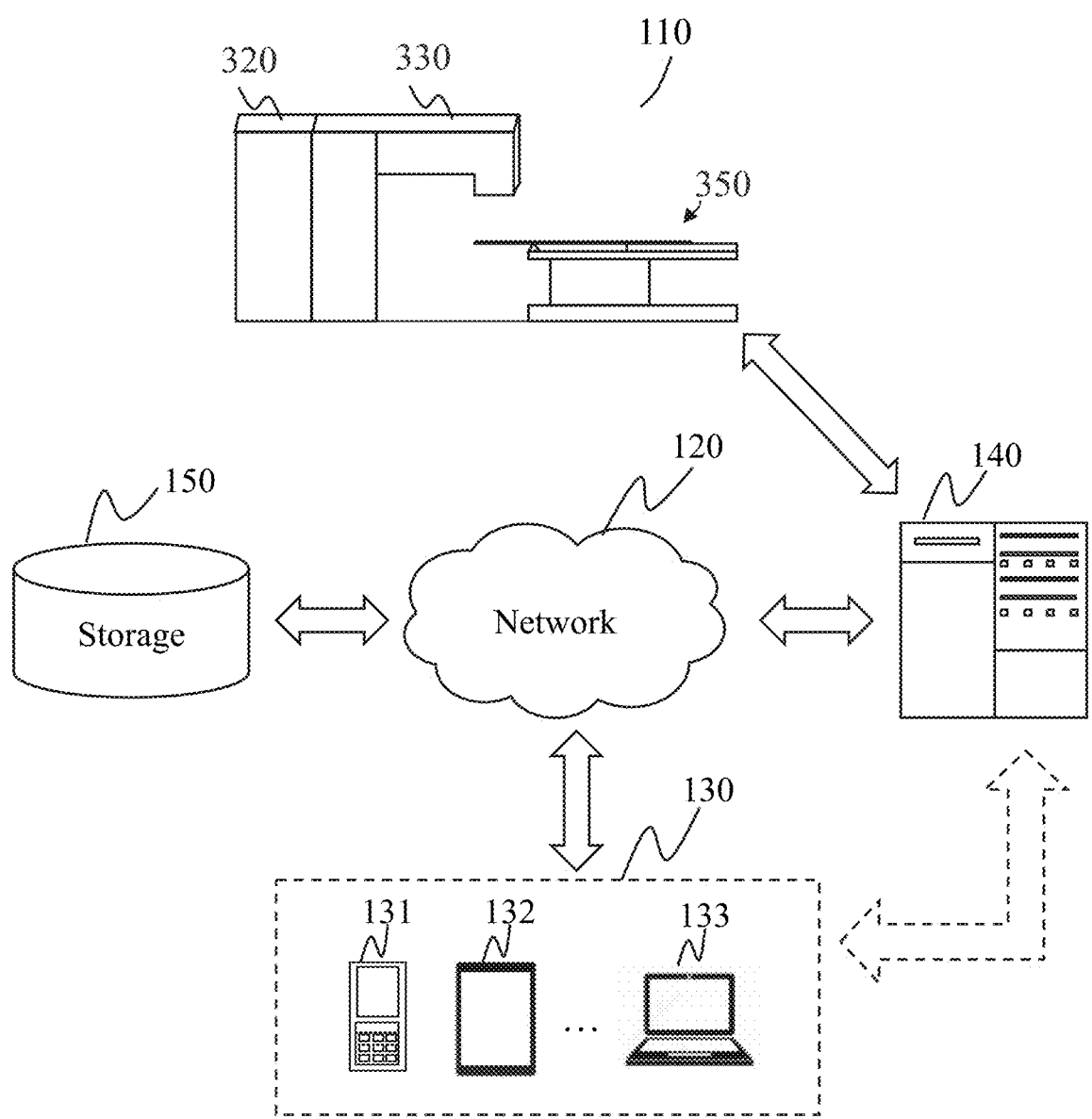

FIG. 1A and FIG. 1B are schematic diagrams illustrating an exemplary diagnostic and treatment system 100 according to some embodiments of the present disclosure. As shown, the diagnostic and treatment system 100 may include an image guided radio therapy (IGRT) apparatus 110, a network 120, one or more terminals 130, a processing engine 140, and a storage 150.

The IGRT apparatus 110 may be a multi-modality (e.g., two-modality) apparatus to acquire a medical image and perform radio therapy. The medical image may be a Computed Tomography (CT) image, a (Magnetic Resonance Imaging) MRI image, an ultrasonic image, a four-dimensional (4D) image, a three-dimensional (3D) image, a two-dimensional (2D) image, a diagnostic image, and a non-diagnostic image, or the like, or a combination thereof. The IGRT apparatus 110 may include one or more diagnostic devices and/or treatment devices. For example, a CT device, a Cone beam CT, a Positron Emission Tomography (PET) CT, a Volume CT, an RT device, and a couch, or the like, or a combination thereof.

In some embodiments, the IGRT apparatus 110 may include a CT device 320, an RT device 330 and a couch 350, or the like, or a combination thereof. The CT device 320 may obtain a CT image of an image object. The RT device 330 may perform radio therapy according to the CT image and other information. The CT device 320 and the RT device 330 may share the couch 350 in a process of image guided radio therapy.

The network 120 may include any suitable network that can facilitate exchange of information and/or data for the diagnostic and treatment system 100. In some embodiments, one or more components of the diagnostic and treatment system 100 (e.g., the IGRT apparatus 100, the terminal 130, the processing engine 140, the storage 150, etc.) may communicate information and/or data with one or more other components of the diagnostic and treatment system 100 via the network 120. For example, the processing engine 140 may obtain image data from the IGRT apparatus 110 via the network 120. As another example, the processing engine 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the diagnostic and treatment system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a GearVR™, etc. In some embodiments, the terminal(s) 130 may be part of the processing engine 140.

The processing engine 140 may process data and/or information obtained from the IGRT apparatus 110, the terminal 130, and/or the storage 150. For example, the processing engine 140 may process image data and determine a regularization item that may be used to modify the image data. In some embodiments, the processing engine 140 may be a single server or a server group. The server group may be centralized or distributed. In some embodiments, the processing engine 140 may be local or remote. For example, the processing engine 140 may access information and/or data stored in the IGRT apparatus 110, the terminal 130, and/or the storage 150 via the network 120. As another example, the processing engine 140 may be directly connected to the IGRT apparatus 110, the terminal 130 and/or the storage 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented by a computing device 200 having one or more components as illustrated in FIG. 2A.

The storage 150 may store data, instructions, and/or any other information. In some embodiments, the storage 150 may store data obtained from the terminal 130 and/or the processing engine 140. In some embodiments, the storage 150 may store data and/or instructions that the processing engine 140 may execute or use to perform exemplary methods described in the present disclosure. In some embodiments, the storage 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage 150 may be connected to the network 120 to communicate with one or more other components in the diagnostic and treatment system 100 (e.g., the processing engine 140, the terminal 130, etc.). One or more components in the diagnostic and treatment system 100 may access the data or instructions stored in the storage 150 via the network 120. In some embodiments, the storage 150 may be directly connected to or communicate with one or more other components in the diagnostic and treatment system 100 (e.g., the processing engine 140, the terminal 130, etc.). In some embodiments, the storage 150 may be part of the processing engine 140.

In some embodiments, one or more components (e.g., the table top 355) in the diagnostic and treatment system 100 may move based on a control instruction. The control instruct may be determined based on information of an image (e.g., a treatment image) or other information (e.g., a character point in the treatment image). Similar modifications should fall within the scope of the present disclosure.

FIG. 2A is a schematic diagram illustrating exemplary hardware and/or software components of an exemplary computing device 200 on which the processing engine 140 may be implemented according to some embodiments of the present disclosure. As illustrated in FIG. 2A, the computing device 200 may include a processor 210, a storage 220, an input/output (I/O) 230, and a communication port 240.

The processor 210 may execute computer instructions (e.g., program code) and perform functions of the processing engine 140 in accordance with techniques described herein. The computer instructions may include, for example, routines, programs, objects, components, data structures, procedures, modules, and functions, which perform particular functions described herein. For example, the processor 210 may process image data obtained from the IGRT apparatus 100, the terminal 130, the storage 150, and/or any other component of the diagnostic and treatment system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both step A and step B, it should be understood that step A and step B may also be performed by two or more different processors jointly or separately in the computing device 200 (e.g., a first processor executes step A and a second processor executes step B, or the first and second processors jointly execute steps A and B).

The storage 220 may store data/information obtained from the IGRT apparatus 100, the terminal 130, the storage 150, and/or any other component of the Diagnostic and treatment system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a Random Access Memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing engine 140 for determining a regularization item.

The I/O 230 may input and/or output signals, data, information, etc. In some embodiments, the I/O 230 may enable a user interaction with the processing engine 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing engine 140 and the IGRT apparatus 100, the terminal 130, and/or the storage 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 2B:
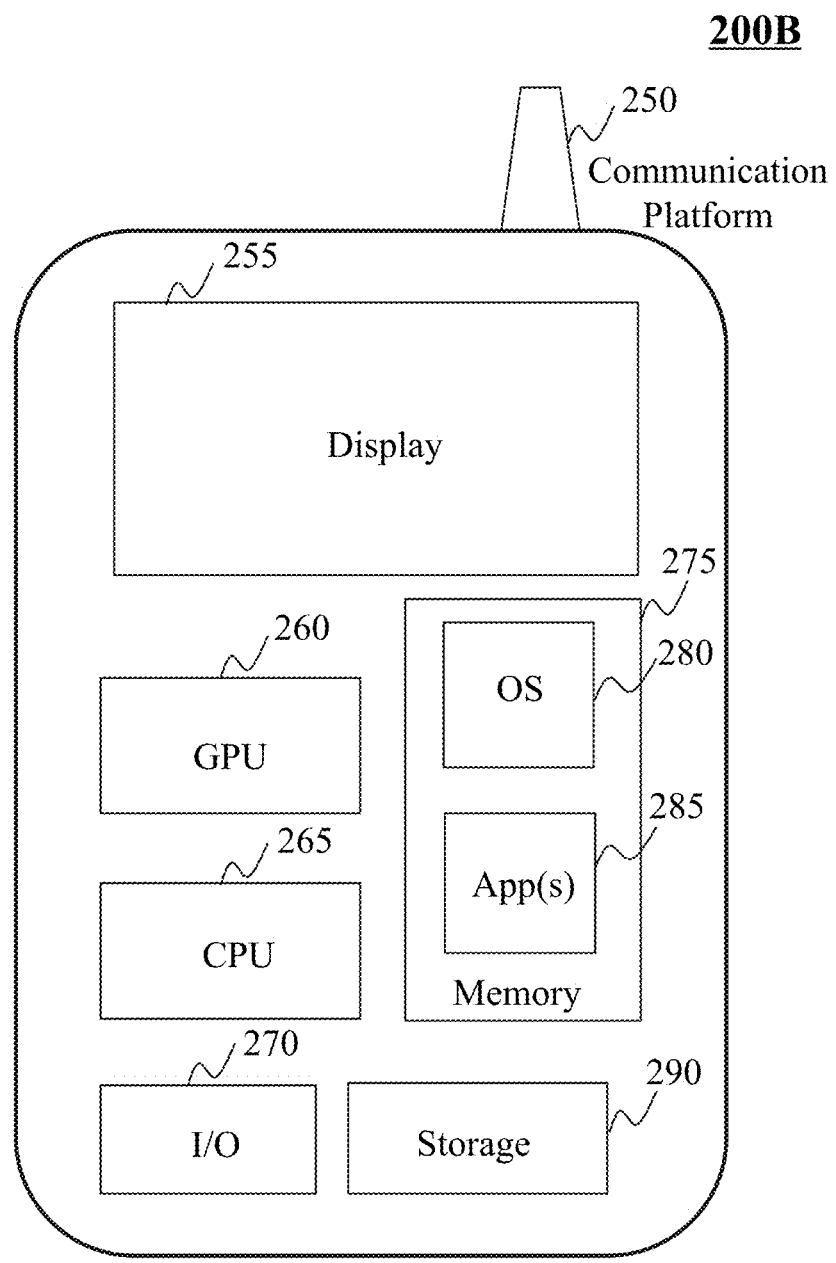
FIG. 2B is a schematic diagram illustrating exemplary hardware and/or software components of an exemplary mobile device on which the terminal may be implemented according to some embodiments of the present disclosure.
Figure 3:
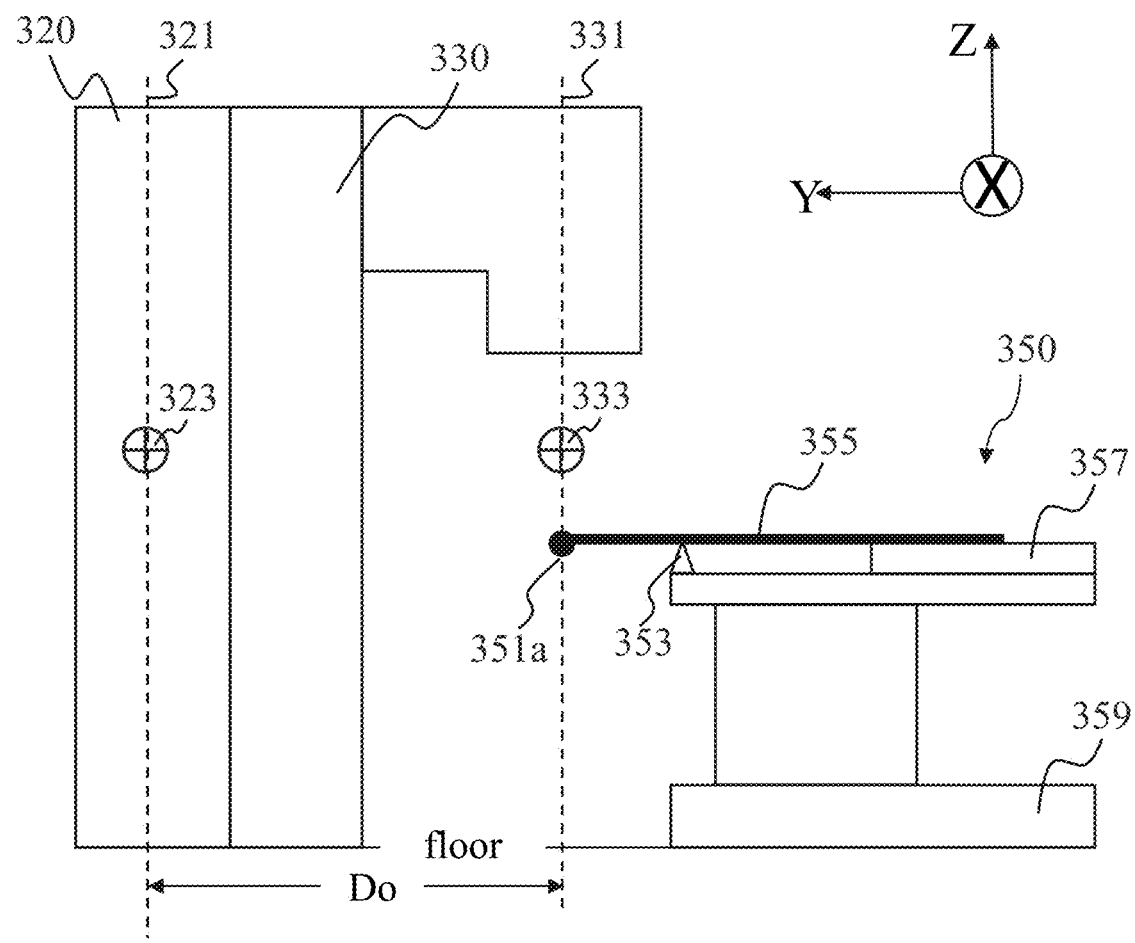
FIG. 3 illustrates a side view of an exemplary RT-CT apparatus and associated components including a couch according to some embodiments of the present disclosure.

FIG. 2B is a schematic diagram illustrating exemplary hardware and/or software components of an exemplary mobile device 200B on which the terminal 130 may be implemented according to some embodiments of the present disclosure. As illustrated in FIG. 3, the mobile device 200B may include a communication platform 250, a display 255, a graphic processing unit (GPU) 260, a central processing unit (CPU) 265, an I/O 270, a memory 275, and a storage 290. In some embodiments, any other suitable component, including but not limited to a system bus or a controller (not shown), may also be included in the mobile device 200B. In some embodiments, a mobile operating system 280 (e.g., IOS™, Android™, Windows Phone™, etc.) and one or more applications 285 may be loaded into the memory 275 from the storage 290 in order to be executed by the CPU 265. The applications 285 may include a browser or any other suitable mobile apps for receiving and rendering information relating to image processing or other information from the processing engine 140. User interactions with the information stream may be achieved via the I/O 270 and provided to the processing engine 140 and/or other components of the Diagnostic and treatment system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

FIG. 3 illustrates a side view of an exemplary RT-CT apparatus and associated components according to some embodiments of the present disclosure. RT-CT apparatus 300 may be an exemplary IGRT apparatus 110 as shown in FIG. 1A and FIG. 1B. RT-CT apparatus 300 may include a CT device 320, an RT device 330, and a couch 350.

Figure 16A:
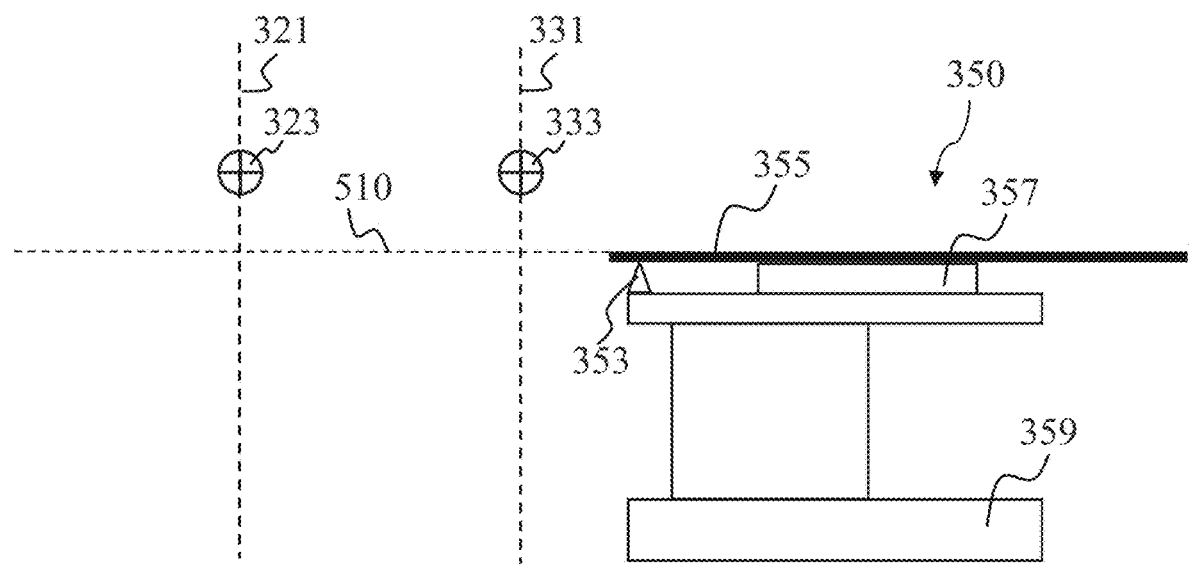
FIG. 16A illustrates the table top at its retracted configuration according to some embodiments of the present disclosure.

The couch 350 may serve to support an object. The object may be a human body (e.g., a patient, etc.), an animal body and a material sample, or the like, or a combination thereof. The couch 350 may move in any direction. For example, a longitudinal direction (i.e., along a long axis of table top 355 in the plane of the table top 355 at its retracted configuration), a lateral direction (i.e., along a short axis of the table top 355 in the plane of the table top 355 at its retracted configuration), or a direction oblique to the longitudinal direction and/or the lateral direction. The movement of the couch 350 may be driven manually or by, for example, a motor. In some embodiments, the longitudinal direction may be described as Y direction. The lateral direction may be described as the X direction. The X direction and the Y direction are within the plane containing the radiotherapy source and the center of rotation of the radiotherapy device and the CT device as illustrated in FIG. 16A and described elsewhere in the present disclosure.

The couch 350 may include a support roller 353, a table top 355, a table top carrier 357, a table base 359, or the like, or a combination thereof. The support roller 353 may support the table top carrier 357. The table top carrier 357 may support the table top 355. The table top 355 may extend along the longitudinal direction of the couch.

In some embodiments, the couch 350 may be used to support an object in a radiation therapy. In some embodiments, the couch 350 may be used to support an object in an imaging process using a CT device. In some embodiments, a CT device and an RT device may share the same couch 350. An object supported on the couch 350 may go through both a CT scanning and a radiation therapy during which the object does not need to change to from one couch to a different couch.

The CT device 320 may obtain a CT image of an object. The RT device 330 may be used for treatment. The RT device 330 may include a Linear Accelerator (LINAC). The CT device 320 and the RT device 330 may be set back to back. The CT device 320 and the RT device 330 may have a same rotation axis. Specifically, the CT device 320 may be mounted on the RT device 330.

A line 321 may correspond to a CT scan plane. A point 323 may be a CT isocenter. The Point 323 may lie on the line 321. A line 331 may correspond to a LINAC source trajectory plane in the side view. A Point 333 may be an LINAC isocenter. The point 333 may lie on the line 331. The point 323 and the point 333 may lie on a same horizontal longitudinal line. The horizontal longitudinal line may be parallel or identical to Y direction. The distance between the point 323 and the point 333 may be indicated as $D_0$.

Figure 4:
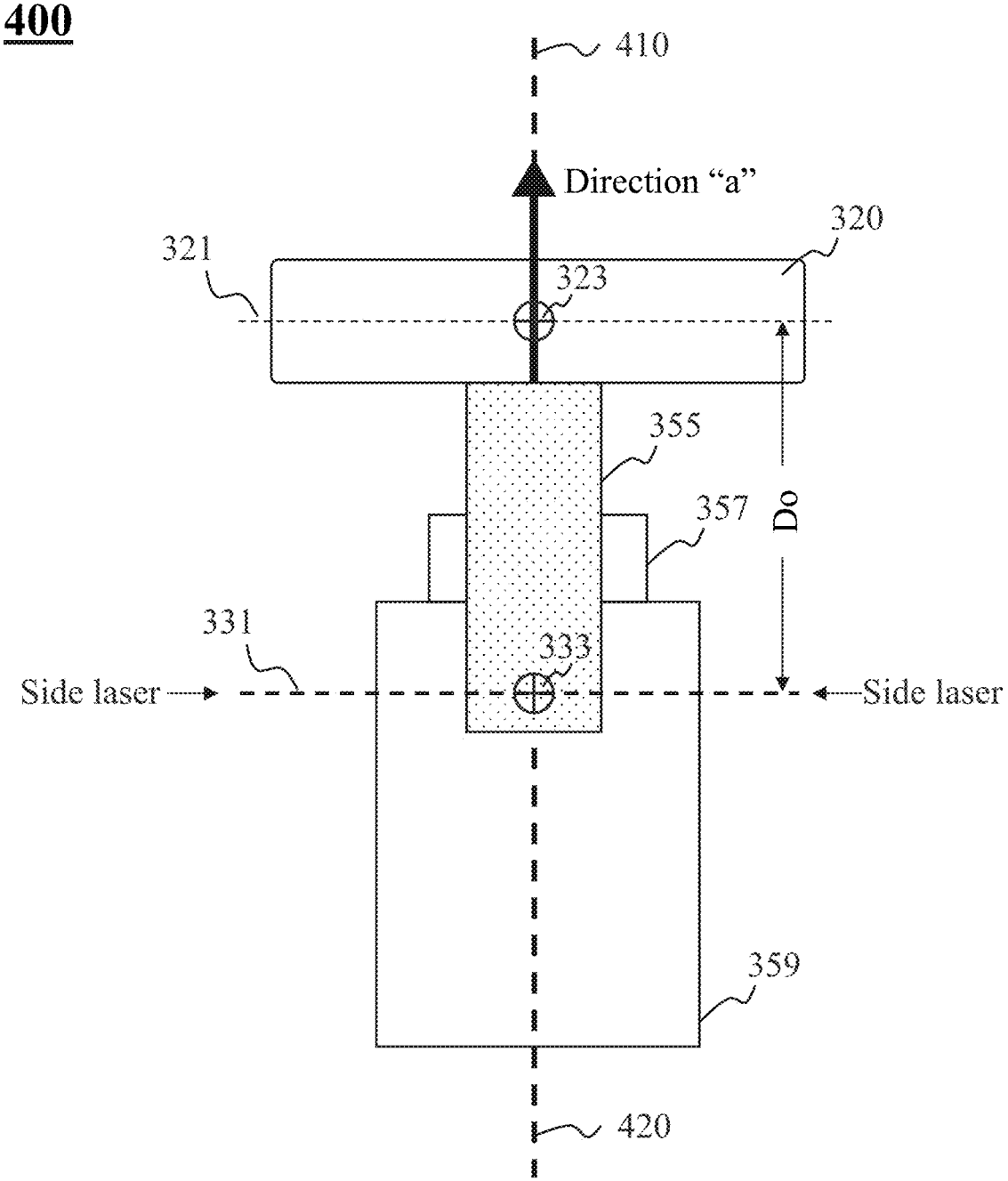
FIG. 4 illustrates a top view of an exemplary RT-CT apparatus and associated components including a couch according to some embodiments of the present disclosure.

FIG. 4 illustrates a top view of an exemplary RT-CT apparatus and associated components according to some embodiments of the present disclosure. An RT-CT apparatus 400 may be an exemplary IGRT apparatus 110 as shown in FIG. 1A and FIG. 1B.

Direction "a" may be a longitudinal direction along which a couch moves. Direction "a" may be parallel or identical to the Y direction as shown in FIG. 3. A line 410 may be normal to both a CT scan plane and an LINAC isocenter plane. A couch 350 may move along the line 410. The angle between direction "a" and the line 410 may be zero. A line 420 may be a longitudinal axis of a table top 355. The angle between direction "a" and the line 420 may be zero. During a treatment, two or more lasers may align with markers (e.g., surface markers) of an object (e.g., a patient, etc.). A line 331 may be a line between two lasers. A point 333 may lie on the line 331. A line 321 and the line 331 may be parallel lines. The Line 410 and the line 420 may be parallel lines. In some embodiments, the line 410 and the line 420 may be a same line.

Figure 5:
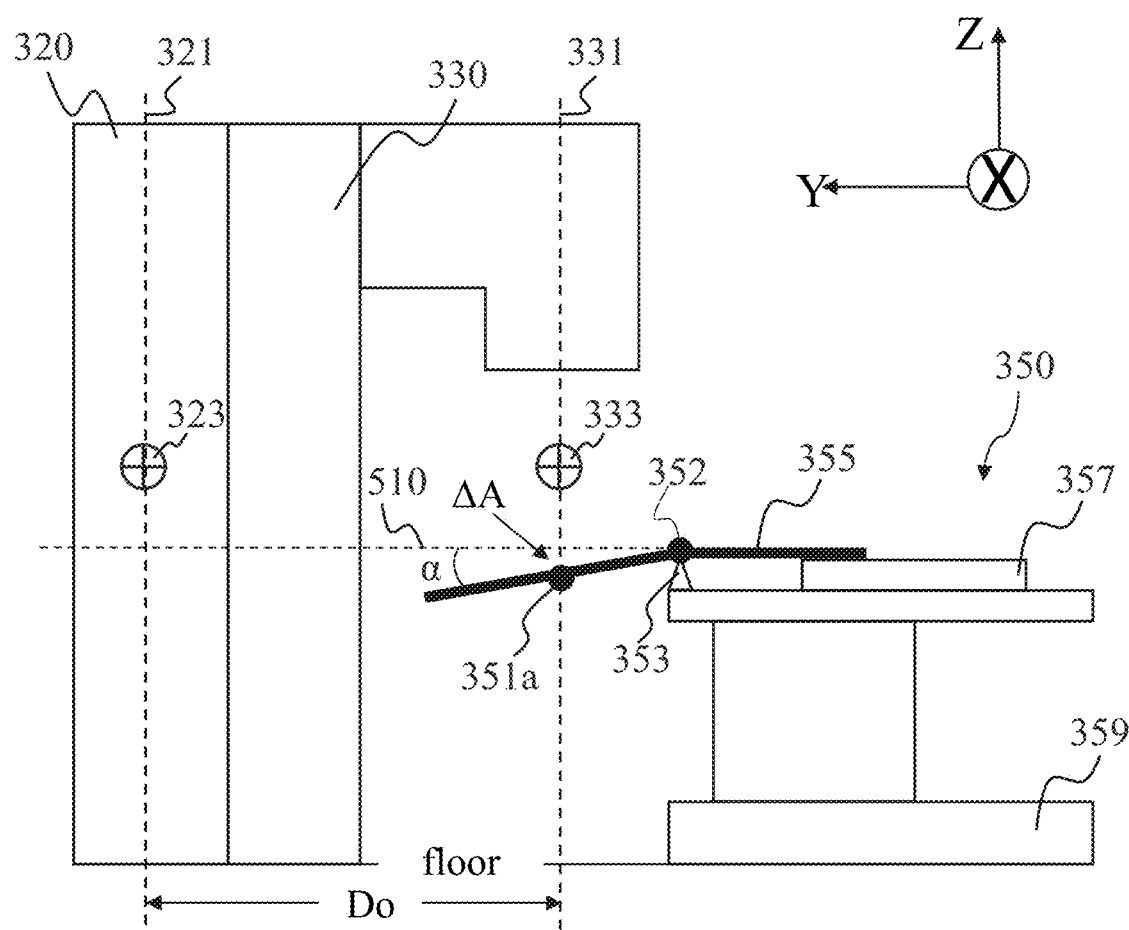
FIG. 5 illustrates a couch sag at an RT position within the RT treatment range of the RT-CT apparatus according to some embodiments of the present disclosure.
Figure 6:
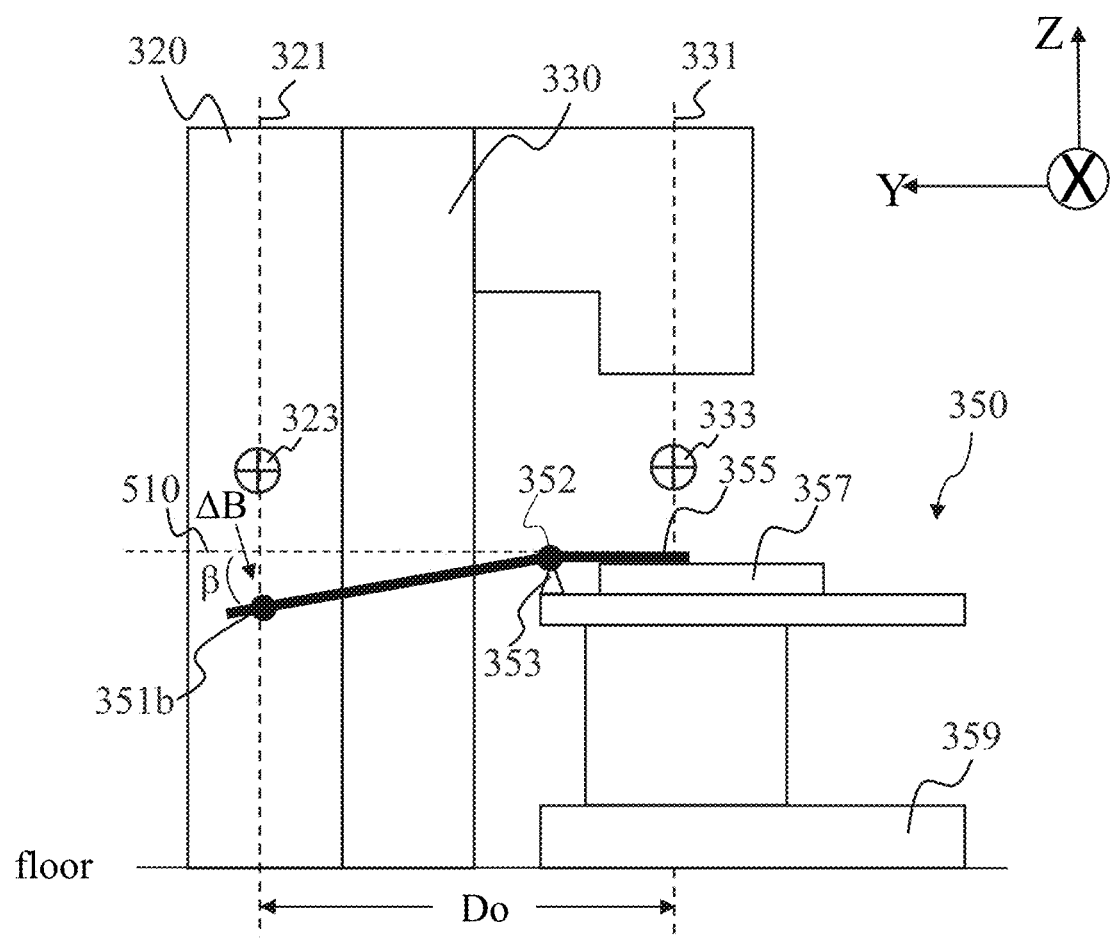
FIG. 6 illustrates a couch sag at a CT position within the CT imaging range of the RT-CT apparatus according to some embodiments of the present disclosure.

FIG. 5 illustrates a couch sag at an RT position within the RT treatment range of the RT-CT apparatus according to some embodiments of the present disclosure. FIG. 6 illustrates a couch sag at a CT position within the CT imaging range of the RT-CT apparatus according to some embodiments of the present disclosure. The RT treatment range may include a plurality of RT working positions at which the RT device may work. The CT imaging range may include a plurality of CT working positions at which the CT device may work. RT-CT apparatuses 500 and 600 may be an exemplary IGRT apparatus 110 as shown in FIG. 1A and FIG. 1B.

While the couch 350 extends from an RT position under the LINAC source of the RT device 330 (as shown in FIG. 5) and then further into the CT device 320 (as shown in FIG. 6), the couch 350 may sag. While the couch 350 retracts in a treatment position under the RT device 330, the sagging of the couch 350 may change. The sagging of a couch may be described in terms of a sagging angle and a sagging amount (e.g., the amount of displacement of a couch in the vertical direction, etc.). The sagging angle may be an angle between the dashed line 510 and the sagging section of the table top 355 of the couch 350 that extends beyond the supporting structure of the table top.

The sagging amount of the table top 355 at a CT position may be the amount by which the table top 355 of the couch 350 sags at a measurement point (e.g., 351b) when the table top 355 is at the CT position. The measurement point 351b may be determined in the space as an intersection of the line 321 and the table top 355. As used herein, a CT position may refer to a position that is within a work area of the CT device 320. When the table top 355 is at a CT position, the line 321 passing through the CT isocenter 323 intersects with the table top 355.

The sagging amount at an RT position may be the amount by which the table top 355 of the couch 350 sags at a measurement point (e.g., 351a) when the table top 355 is at the RT position, as shown in FIG. 5. The measurement point 351a may be determined in the space as an intersection of the line 331 and the table top 355. As used herein, an RT position may refer to a position that is within a work area of the RT device 330. When the table top 355 is at an RT position, the line 331 passing through the RT isocenter 333 intersects with the table top 355. For instance, an RT position may include one under the LINAC source.

In some embodiments, the sagging at an RT position may be described by ($\alpha$, $\Delta A$) as shown in FIG. 5. $\alpha$ may represent the sagging angle of the couch 350 at an RT position, and $\Delta A$ may represent the sagging amount of the couch 350 at the RT position at the measurement point 351a.

In some embodiments, the sagging of the couch at a CT position may be described by ($\beta$, $\Delta B$) as shown in FIG. 6. $\beta$ may represent the sagging angle of the couch 350 at a CT position, and $\Delta B$ may represent the sagging amount of the couch 350 at the CT position at the measurement point 351b.

In some embodiments, the sagging of a couch (or referred to as couch sag, or a sag of the table top) at a position of the couch may be defined as a deviation of the table top at that position from a reference height. The reference height of the table top of the couch may be the height of the table top at its retracted position (as shown in FIG. 16A) when it is supported by its supporting structure. The table top may move up and down in the vertical direction so that the reference height may change. The deviation at a position of the table top from its reference height may occur when at least a portion of the table top extends, along the height direction, beyond the supporting structure of the table top of the couch. When the couch or its table top is unloaded, a deviation may occur due at least partially to the weight of the table top. When the couch or its table top is loaded, a deviation may occur due at least partially to the weight of the table top in addition to the weight of an object that is lying or otherwise placed on the table top of the couch. As used herein, a loaded couch or table top may refer to the situation in which an object is lying or otherwise placed on the table top of the couch. As used herein, an unloaded couch or table top may refer to the situation in which no object is placed on the table top of the couch. For example, the couch sag at a first measure point 351a may be a vertical distance from the table top 355 at the first measurement point 351a to the dashed line 510 as shown in FIG. 5. As another example, the couch sag at a second measure point 351b may be a vertical distance from the table top 355 at the second measurement point 351b to the dashed line 510.

Figure 7:
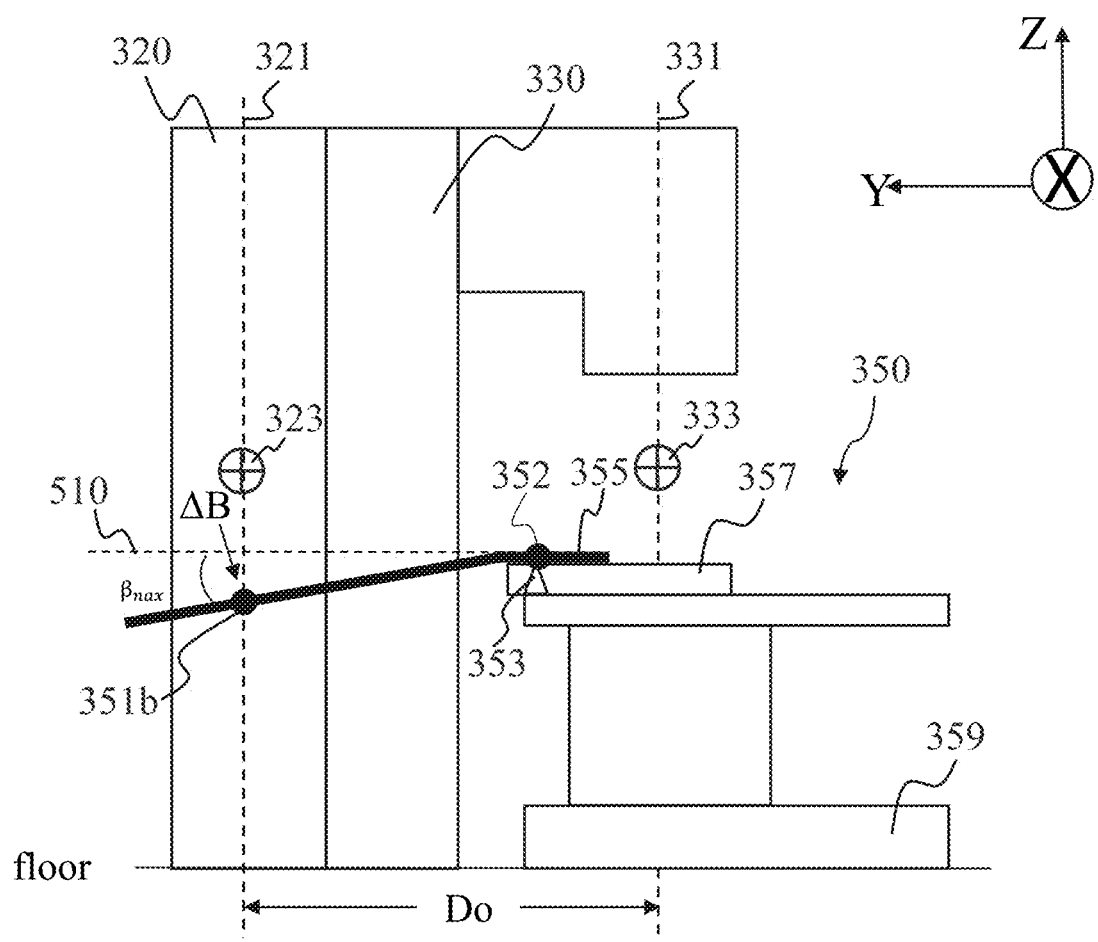
FIG. 7 illustrates a couch sag at a CT position according to some embodiments of the present disclosure.
Figure 16B:
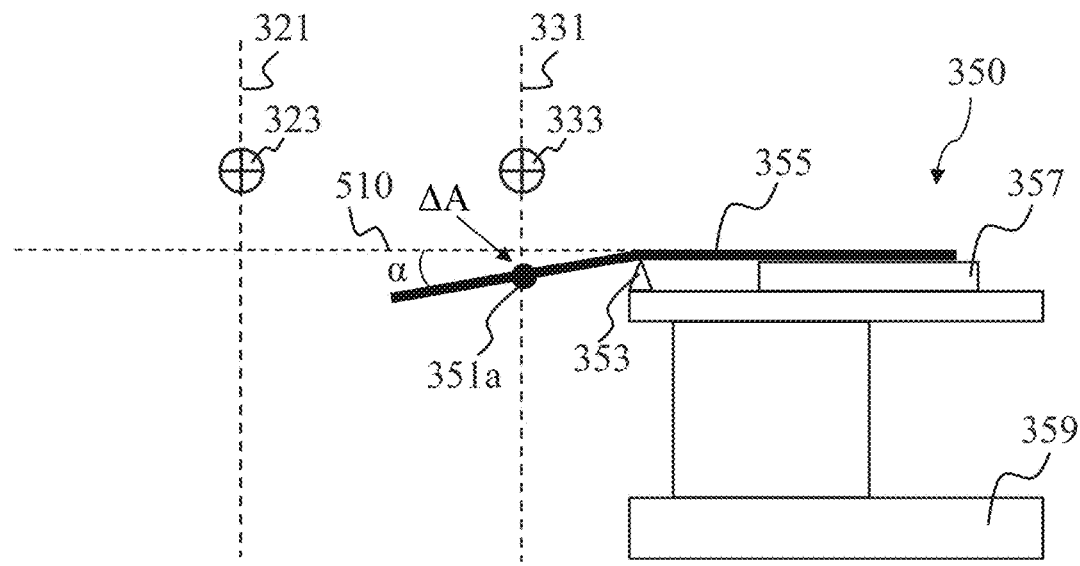
FIG. 16B, FIGS. 16C, and 16D illustrate partially extended configurations of the table top according to some embodiments of the present disclosure.
Figure 16C:
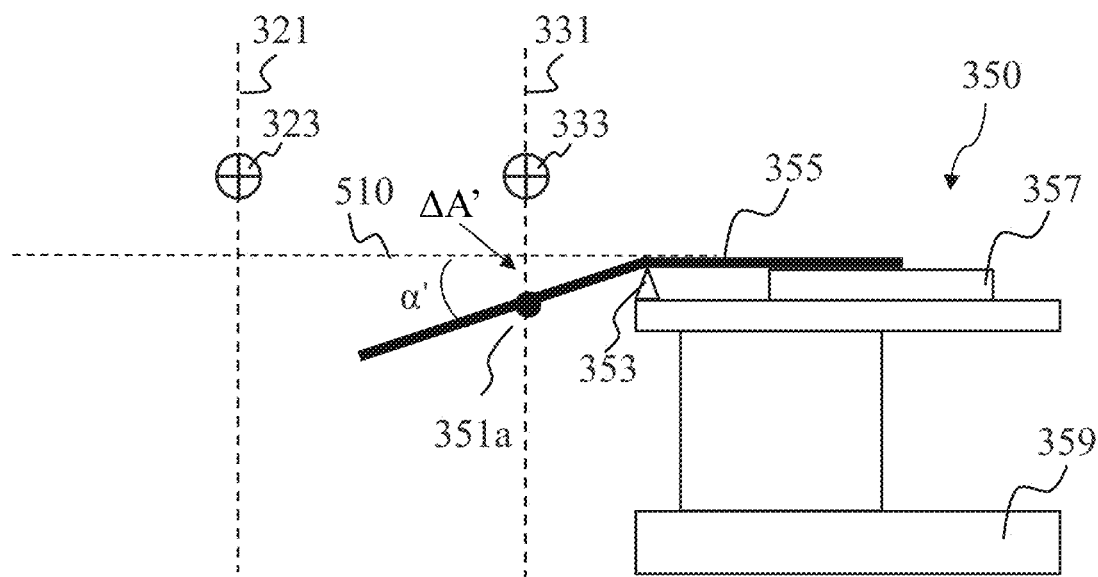

The table top of the couch 350 may have a plurality of configurations including a retracted configuration, a partially extended configuration, and an extended configuration. As used herein, the retracted configuration of the table top of the couch 350 may refer to the condition when the table top is fully retracted to its resting position as shown in FIG. 3 and FIG. 16A. As used herein, the extended configuration of the table top of couch 350 may refer to the condition when the table top is fully extended as shown in FIG. 7 and FIG. 16E. As use herein, a partially extended configuration may refer to the condition of the table top when the table top is partially extended between its retracted configuration and its extended configuration as shown in FIG. 5, FIG. 6, FIG. 16B, FIG. 16C, and FIG. 16D.

The reference height may be indicated as a line, illustrated by the dashed line 510 in FIGS. 5-8 that may be parallel to an isocenter line connecting the CT isocenter 323 and the LINAC isocenter 333. In some embodiments, the isocenter line connecting the CT isocenter 323 and the LINAC isocenter 333 may be horizontal. The dashed line 510 may be a line parallel to the isocenter line. A support point (e.g., point 352 in FIG. 5) on the table top 355 by, for example, support roller 353 may lay on the dashed line 510, if the thickness of the table top 355 is neglected. Reference height H may be the distance between the dashed line 510 and the isocenter line in the vertical direction. The dashed line 510 may be a line of the table top when the table top is unloaded. As used herein, reference height H may be the distance between the unloaded table top and the isocenter. According to IEC 61217 that is applicable to equipment and data related to the process of teleradiotherapy, when the support point on the table top 355 by, for example, the support roller 353 falls on the isocenter line, H is 0; H is positive when the support point is above the isocenter line and negative when the support point is below the isocenter line when taking a point on the isocenter line as an origin. In the examples illustrated in FIG. 5 and FIG. 6, H increases when couch 350 moves upwards.

In some embodiments, the height G, at a measurement point, of a loaded couch may be defined as a vertical deviation of the table top 355, at the measurement point 351 (e.g., a first measurement point 351a and a second measurement point 351b), from the isocenter line. As used herein, height G may be the distance between the loaded table top and the isocenter. When the table top 355 at the measurement point 351 aligns with the isocenter line, G is 0; G is positive when the table top 355 at the measurement point 351 is above the isocenter plane; G is negative when the table top 355 at the measurement point 351 is below the isocenter plane. In the examples illustrated in FIG. 5 and FIG. 6, G increases when the couch 350 moves upwards.

Figure 8:
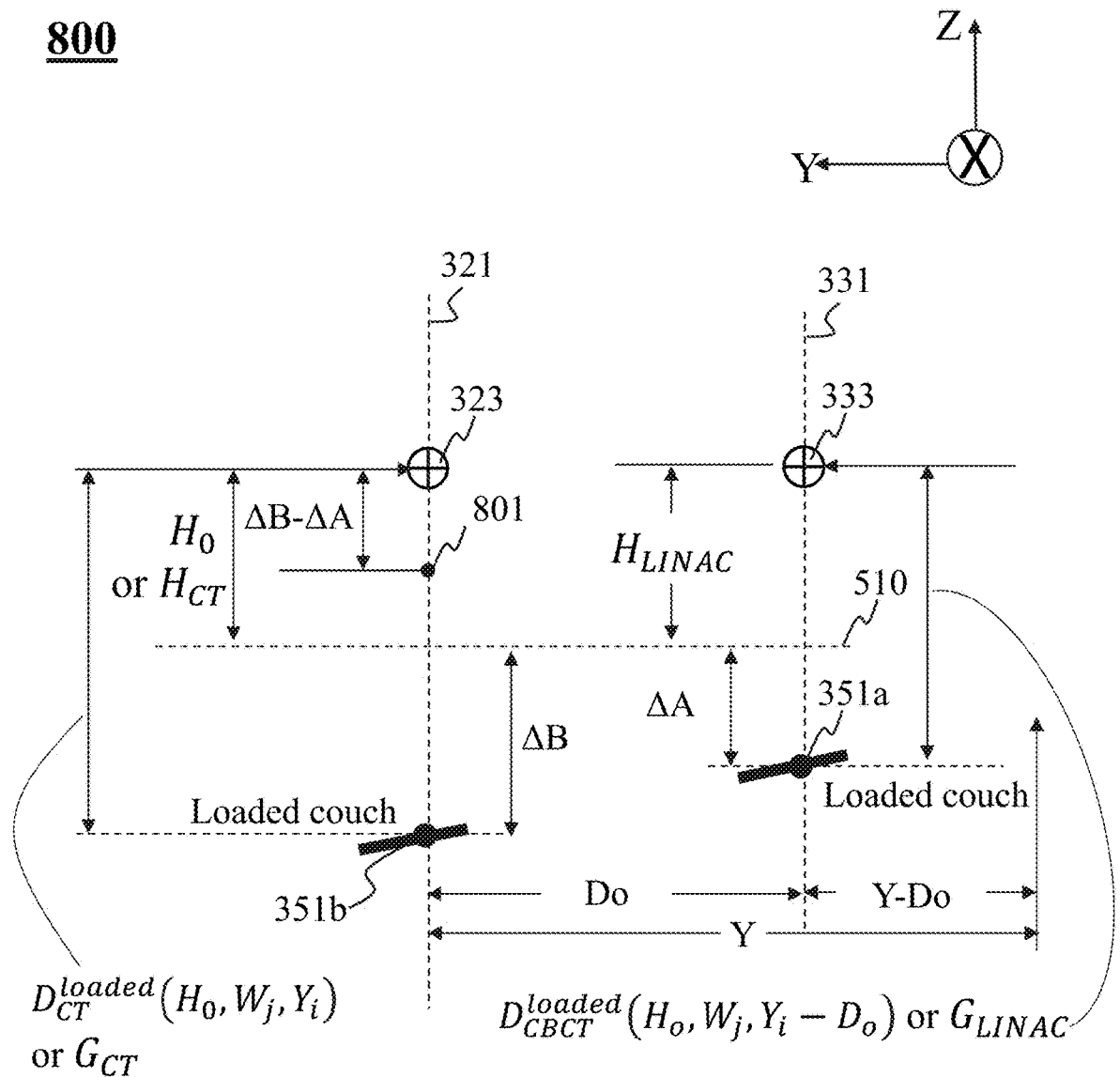
FIG. 8 illustrates a schematic diagram of a couch sag difference between an RT position and a CT position according to some embodiments of the present disclosure.

In some embodiments, couch sag $\Delta A$ at a LINAC isocenter (i.e., at the measurement point 351a) as shown in FIG. 5 and FIG. 8 may be described through Equation (1) below:

$$\Delta A = H_{LINAC} - G_{LINAC}, \tag{1}$$

in which $H_{LINAC}$ refers to the reference height of the table top when the table top is unloaded at a specific RT position, and $G_{LINAC}$ refers to the height of the table top at the measurement point 351a when the table top is loaded at the specific RT position.

In some embodiments, couch sag ΔB at a CT isocenter (i.e., at the measurement point 351b) as shown in FIG. 6 and FIG. 8 may be described through Equation (2) below:

$$\Delta B = H_{CT} - G_{CT}, \quad (2)$$

in which $H_{CT}$ refers to reference height of the table top when the table top is unloaded at a specific CT position, and $G_{CT}$ refers to the height of the table top at the measurement point 351b when the table top is loaded at the specific CT position.

In some embodiments, the amount of a couch sag at a position (or a measurement point) may be a function of the weight (or the weight distribution) of an object lying or otherwise placed on the table top 355 of the couch 350 (or referred to as a loaded object), the weight (or the weight distribution) of the table top 355 of the couch 350, and the extent to which the table top 355 of the couch 350 is extended, and the location of point on the table top at the measurement point (e.g., the distance between the point on the table top at a measurement position and the origin of the table top along the longitudinal direction). In some embodiments, the origin may be fixed with respect to the table top. In some embodiments, the origin may move when the table top moves. In some embodiments, the origin may be fixed with respect to the supporting structure on the couch that may provide support for the table top. For instance, the origin may be located at the end of the table top that is always supported by or in direct contact with a supporting structure (e.g., table top carrier 357) of couch 350. In some embodiments, the impact of the variation in weight distribution among different loaded objects may be ignored.

In some embodiments, reference height H and/or the height of a loaded couch may be determined based on an image (e.g., a CT image, a CBCT image, etc.), measured by a sensor, retrieved form a database, or the like, or a combination thereof.

FIG. 7 illustrates a couch sag at a CT position according to some embodiments of the present disclosure. An RT-CT apparatus 700 may be an exemplary IGRT apparatus 110 as shown in FIG. 1A and FIG. 1B.

In some embodiments, the sagging of the portion of the table top located between its origin and support roller 353 may be neglected. The sagging of the portion of the table top extending beyond support roller 353 may change as the table top extends or retracts. An amount of extension may be used to describe the displacement of the table top form a first position (e.g., a position corresponding to the retracted configuration as shown in FIG. 3 and FIG. 16A) to a second position (e.g., a position corresponding to a partially extended configuration as shown in FIG. 5, FIG. 6, and FIGS. 16B, 16C and 16D). For example, the amount of extension may be zero when the table top 355 is at its retracted configuration as shown in FIG. 16A. The amount of extension may increase when the table top moves from the retracted configuration towards its extended configuration (as shown in FIG. 16E) in the Y direction. The sagging angle and/or the sagging amount at a measurement point (e.g., 351a, 351b, etc.) may increase along with the increase of the amount of extension. For example, the amount of extension of the table top 355 in its configuration illustrated in FIG. 16E is greater than the amount of extension of the table top 355 in its configuration illustrated in FIG. 16B; the sagging angle (e.g., α') and/or the sagging amount (e.g., ΔA') when the table top is in its configuration as shown in FIG. 16C may be greater than the sagging angle (e.g., α) and/or the sagging amount (e.g., ΔA) when the table top is in its configuration as shown in FIG. 16B. When table top 355 moves to a characteristic position so far that the support roller 353 may barely influence the deflection of table top 355, angle β may reach a maximum value $\beta_{max}$.

It should be noted that RT-CT apparatus 300, 400, 500, and 600 described herein are provided for the purposes of illustration, and not intended to limit the scope of the present disclosure. Apparently for persons having ordinary skills in the art, numerous variations and modifications may be conducted under the teaching of the present disclosure. However, those variations and modifications do not depart the scope of the present disclosure. For example, couch 350 may include one or more sensors. The one or more sensors may be used to measure a couch sag, reference height of couch 350, etc. Similar modifications fall within the scope of the present disclosure.

FIG. 8 illustrates a schematic diagram of a couch sag difference between an RT position and a CT position according to some embodiments of the present disclosure. The couch sag difference may be between the couch sag at a first measurement point when the table top is at an RT position and the couch sag at a second measurement point when the table top is at a CT position.

In some embodiments, a three-dimensional coordinate system may be used in the diagnostic and treatment system 100. A first axis may be parallel to the longitudinal direction of the table top 355 (e.g., the Y direction as shown in FIG. 3), a second axis may be parallel to the lateral direction of the table top (e.g., the X direction perpendicular to and pointing out of the paper as shown in FIG. 3), a third axis may along a vertical direction (also referred to as the Z direction as shown in FIG. 3) that is perpendicular to the plane of the table top 355 when the table top 355 is at its retracted position. The origin of the three-dimensional coordinate system may be any point in the space. The origin of the three-dimensional coordinate system may be determined by a user. The origin of the three-dimensional coordinate system may be determined by the diagnostic and treatment system 100. In some embodiments, the origin of the three-dimensional coordinate system may be at point 352 as shown in FIGS. 5-7, such that the coordinates of the measurement point 351a may be (L, Y*, $-D_o$, h), and the coordinates of the measurement point 351b may be (L', Y*, h') in the three-dimensional coordinate system. According to the movement of the couch 350 from an RT position to a CT position in the X direction, L and L' may be the same or different. According to the movement of the couch 350 from an RT position to a CT position in the Y direction, h and h' may be the same or different.

Point 801 may be a second characteristic point on a treatment CT image. The point 801 may not be identified before couch sag is measured. The second characteristic point on the treatment CT image may be a point on a treatment CT image corresponding to an internal anatomical point (e.g., a point of a tumor, etc.) of the object. In some embodiments, according to the second characteristic point an image registration may be performed (as exemplified in process 1000). In a treatment procedure, the second characteristic point on a treatment CT image and a first characteristic point on a planning CT image may be determined so that the treatment CT image may be registered with the planning CT image. The treatment CT image may be an image used in the treatment procedure. The treatment CT image may show the situation of the object at the time the treatment CT image is taken. For example, the treatment CT may describe the position and/or the size of a tumor of the patient.

In an IGRT procedure, an initial setup may be performed. In the initial setup of an object (e.g., a patient), the patient may lie or otherwise be placed on the table top 355 of the couch 350. The one or more surface markers on the object and laser beams may be used to position the patient such that an internal anatomical point (e.g., a target portion of the patient) may align with the RT isocenter. The internal anatomical point may correspond to the first characteristic point in the planning CT image. The first characteristic point of the planning CT image may be substantially aligned with the RT isocenter or spaced by a certain distance from the RT isocenter. The first character point and/or the distance may be determined by a physicist or determined by a processor of the diagnostic and treatment system 100.

After the initial setup, a treatment CT image may be obtained by moving the table top 355 of the couch 350 according to a vector $\vec{v}$. The vector $\vec{v}$ may represent a displacement of the table top 355 of the couch 350 from an RT position to a CT position. In the treatment CT image, the second characteristic point may need to be identified. In some embodiments, the second characteristic point may be displayed on the display 255 of the mobile device 200B as described in FIG. 2B after the second characteristic point is identified.

In some embodiments, the second characteristic point of the object may be determined based on one or more surface markers on the object. The surface markers may correspond to the internal anatomical point of the object. For example, the lasers of the RT device 330 may be aligned with the surface markers (e.g. cross-lines arranged on the object in X, Y, and Z directions), so that the LINAC isocenter of the RT device 330 may align with the internal anatomical point of the object. It is suitable for this solution that the mentioned surface marker is not radio-opaque. The LINAC isocenter of the RT device 330 may relate to the arrangement of the one or more lasers of the RT device 330.

In some embodiments, a treatment CT image may be taken non-in situ (i.e. $\vec{v} \neq 0$). For example, the treatment CT image may be taken by CT device 320 after the table top carrying the patient is moved by $\vec{v}$ after the initial setup.

Merely by way of example, to move the patient to a CT position for the non-in situ treatment CT, the table top of the couch may need to be moved by l along the lateral direction (i.e., parallel to the second axis), and Δh along the vertical direction (i.e., parallel to the third axis) from the initial set-up position of the table top as shown in FIG. 8. A longitudinal distance in the Y direction between the CT isocenter 323 and the LINAC isocenter 333 may be described as $D_o$ as shown in FIGS. 3-8. Therefore, the vector $\vec{v}$ from the initial setup position (e.g., an RT position) to the CT position may be shown in Equation (3) below:

$$\vec{v}=(l,D_0,\Delta h). \quad (3)$$

The lateral offset l may be positive or negative, indicating that the lateral movement of the table top is to the left or right from its initial setup position. The vertical offset Δh may be positive or negative, indicating that the movement of the table top is upward or downward from its initial set-up position.

The table top 355 of the couch 350 may be moved by $D_o$ from an RT position to a CT position. In some embodiments, the couch sag may be zero (e.g., when the couch is unloaded and the weight of the couch may be ignored). A second characteristic point on the treatment CT slice corresponding to the internal anatomical point within the object (e.g., a patient) may be represented in a treatment CT slice taken at a vertical offset Δh from the LINAC isocenter 333, a lateral offset l from the LINAC isocenter 333 and a longitudinal offset $D_o$. from the LINAC isocenter 333. In some embodiments, the couch sag may be ΔB−ΔA. A second characteristic point on the treatment CT slice corresponding to the internal anatomical point within the object (e.g., a patient) may be represented in a treatment CT slice taken at a vertical offset Δh+ΔB−ΔA from the LINAC isocenter 333.

After a treatment CT image is acquired, the table top 355 of the couch 350 may move back by vector $-\vec{v}$ to align the internal anatomical point with the LINAC isocenter 333. Then a treatment may be performed based on a registration between a planning CT and the treatment CT. Descriptions of the registration between the planning CT and the treatment CT may be found elsewhere in the present disclosure. See, for example, FIG. 10 and the descriptions thereof.

However, the table top 355 of the couch 350 may sag further when travelling from LINAC isocenter 333 to CT isocenter 323 (where the treatment CT image is acquired) and may recover when it travels back. As illustrated in FIG. 6, the internal anatomical point of a patient represented in a treatment CT slice acquired at a CT position (at a couch longitudinal position $Y_*$) may move vertically up by (ΔB (., Y*)−ΔA(., Y*−$D_o$)) at a couch longitudinal position (Y*−$D_o$) when the table top 355 of couch 350 is retracted to an RT position without considering the movement of the couch in the Z direction (e.g., Δh). As used herein, ΔB may represent the sagging amount of the table top 355 of the couch 350 at the measurement point 351b when the table top 355 is at a CT position. As used herein, ΔA may represent the sagging amount of the table top 355 of the couch 350 at the measurement point 351a when the top table 355 is at an RT position. That is, in a treatment CT image, the CT scanning center (e.g., the geometrical center of the CT image) may be located below the position of the table top 355 at the measurement point 351a (when the table top 355 is at the RT position after the initial setup) by an amount Δh+(AB (., Y*)−ΔA(., Y*−$D_o$)) at the measurement point 351b (at a couch longitudinal position Y*), due at least partially to the couch sagging. The internal anatomical point may be represented in the same slice taken at a vertical offset (i.e., Δh+ΔB (., Y*)−ΔA(., Y*−$D_o$).) and at a lateral offset l away from the identified CT scanning center. That is, the second characteristic point may be located in the slice described by Equation (4-1).

In some embodiments, a vertical coordinate of the CT machine isocenter in the Z direction may be $T_{CT\,MI}$, and a vertical coordinate of the second characteristic point in the Z direction may be $T_{CP}$. In some embodiments, $T_{CP}$ may be described using Equation (4) below:

$$T_{CP}=T_{CT\,MI}+(\Delta h-((\Delta B-\Delta A)). \quad (4-1)$$

In some embodiments, a CT scanning center (e.g., the geometrical center of the CT image) may deviate from the CT isocenter by a vector $\vec{v}_1$ in the CT scan plane. The second characteristic point Tx Iso (h, l) may be described using Equation (4-2) below:

$$Tx\,Iso(h,l)=\vec{v}_1+(l,\Delta h-(\Delta B-\Delta A)). \quad (4-2)$$

Figure 9A:
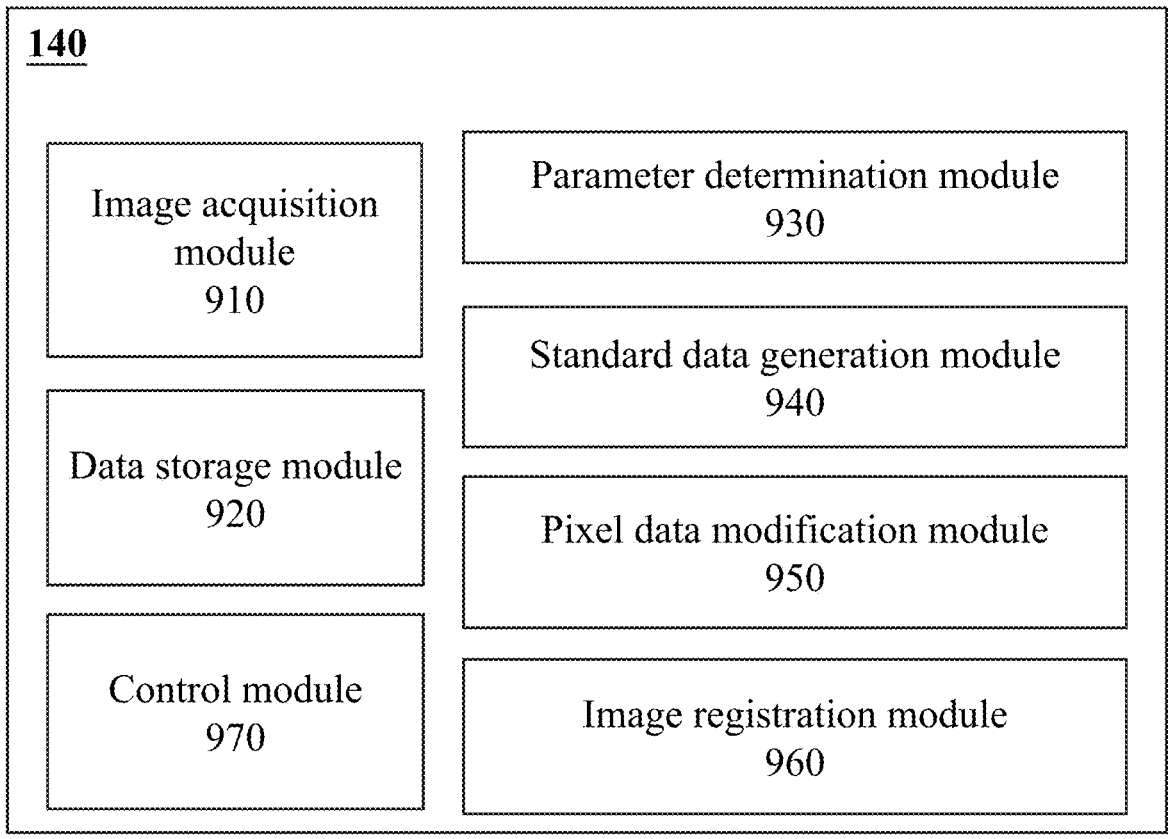
FIG. 9A illustrates an exemplary image processing apparatus according to some embodiments of the present disclosure.

FIG. 9A illustrates an exemplary image processing apparatus according to some embodiments of the present disclosure. Processing engine 140 may include an image acquisition module 910, a data storage module 920, a parameter determination module 930, a standard data generation module 940, a pixel data modification module 950, an image registration module 960, and a control module 970. Components in the processing engine 140 may be connected to or communicate with each other and/or other components in diagnostic and treatment system 100, for example IGRT apparatus 110, terminal 130, processing engine 140, and storage 150, or the like, or a combination thereof. The processing engine 140 may be implemented on the computing device 200 as illustrated in FIG. 2A.

The image acquisition module 910 may obtain an image. The image may be acquired by the IGRT apparatus 110, generated by the processing engine 140, or retrieved from another source (e.g., the storage 150, a storage, etc.) The image may be a planning CT image or a treatment CT image. As used herein, a planning CT image may be a CT image generated by a planning CT scan and mark with a treatment plan (e.g., determining areas that need treatment and outlining areas where radiation needs to be limited or avoided completely) by a physician and/or radiotherapy specialist. The treatment CT image may be a pre-treatment CT image, during-treatment CT image, a post-treatment CT image, etc. The treatment CT image may provide position information regarding the region of interested (such as the target area) before/during/after treatment. In some embodiments, the treatment CT image may be aligned with a planning CT image.

The data storage module 920 may store data. The data may be image data (e.g., a planning CT, a treatment CT, etc.), height data (e.g., a reference height of the table top, a height of the table top at a position, etc.), position data (e.g., a longitudinal position, etc.), parameter data (e.g., a treatment parameter, a treatment verification parameter, etc.), or the like, or a combination thereof. The data may be obtained by the IGRT apparatus 110 (e.g., a treatment CT image, height data acquired by a sensor, etc.) or retrieved from another source (e.g., the network 160, the storage 150, and the terminal 130, the data storage module 920, etc.).

The parameter determination module 930 may determine one or more parameters. The parameter may be a position parameter, a treatment parameter, and a treatment verification parameter, or the like, or a combination thereof. For example, the parameter may relate to a couch sag used to correct an image. As another example, the parameter may be a second characteristic point on a treatment CT image. The second characteristic point and a first characteristic point on a planning CT image may be used for registering the planning CT image with the treatment CT image.

Figure 9B:
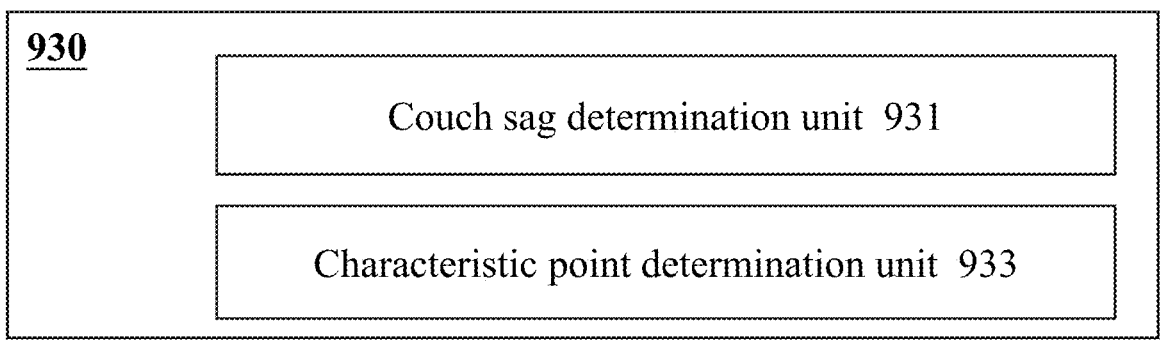
FIG. 9B illustrates an exemplary parameter determination module according to some embodiments of the present disclosure.

In some embodiments, the parameter determination module 930 may include a couch sag determination unit 931 and a characteristic point determination unit 933 as shown in FIG. 9B. More details descriptions of the parameter determination module 930 may be found in FIG. 9B.

The standard data generation module 940 may generate standard data. The standard data may include a first standard parameter relating to a first modality (e.g., at an RT position, etc.) and a second standard parameter relating to a second modality (e.g., at a CT position, etc.). The standard data may describe a relationship among a couch sag, the longitudinal position of the table top at a measurement point, the amount of the extension of the table top, and a loaded weight. The relationship may be described in the form of a table, a function, a graph, or the like, or a combination thereof. The longitudinal position of the table top at a measurement point may refer to the point on the table top at a measurement position, or the distance between the point and the origin of the table top along the longitudinal direction.

Table A shows standard data describing an exemplary relationship among a CT couch sag, the longitudinal position of a measurement point (e.g., a measurement point corresponding to a surface marker of an object lie on the table top 355, any point selected by a user of the table top 355, the origin of the table top 355, etc.) at a CT position, and a loaded weight. As used herein, the longitudinal position of a measurement point may be the distance in the longitudinal direction from the measurement point to a reference point (e.g., the origin of the table top, etc.). Table A may include couch sags at the measurement point 351b corresponding to the CT isocenter for different weights and longitudinal positions. At one configuration of the table top when the table top is extended to a position, different longitudinal positions and/or loaded weights may correspond to different CT couch sags. At different configurations of the table top corresponding to different amounts of extension, the measurement point 351b may correspond to different longitudinal positions. Based on the structural information regarding the table top 355, the couch 350, the CT device 320 and the RT device 330, when the table top 355 is moved to a position, the longitudinal position of the point of the table top corresponding to a measurement point (e.g., 351a, 351b, etc.) may be determined.

TABLE A

Couch sag at the CT isocenter for different weights and longitudinal positions

| | W = 0 | $W_1$ | $W_2$ | ... | $W_j$ | ... | $W_N$ |
|---|---|---|---|---|---|---|---|
| $Y_1$ | $D_{CT}^{unloaded}(H_o, Y_1)$ | | | | | | |
| $Y_2$ | $D_{CT}^{unloaded}(H_o, Y_2)$ | | | | | | |
| ... | | | | | | | |
| $Y_i$ | | | | | $\Delta B(W_j, Y_i)$ | | |
| ... | | | | | | | |
| $Y_N$ | $D_{CT}^{unloaded}(H_o, Y_N)$ | | | | | | |

As shown in Table A, $Y_N$ refers to a longitudinal position at the measurement point 351b corresponding to the CT isocenter when the table top is at a CT position. $W_j$ refers to a weight loaded on a couch. The longitudinal position (e.g., $Y_1$, $Y_2$, $Y_3$, $Y_N$, etc.) of the measurement point and the loaded weight (e.g., $W_1$, $W_2$, $W_3$, $W_N$, etc.) may be zero or a positive number. For example, the longitudinal position of the measurement point of the table top 355 may be 800 mm, 2300 mm, or the like. For example, the loaded weight may be 54 kg, 55 kg, 56 kg, 59.5 kg, and 100 kg, or the like.

$D_{CT}^{unloaded}(H_o, Y_N)$ refers to a distance in the vertical direction between the table top at the measurement point 351b (corresponding to the longitudinal position $Y_N$) and the CT isocenter 323 without a loaded weight, when the reference height is $H_o$.

$\Delta B(W_j, Y_i)$ refers to a couch sag at the measurement point 351b at a longitudinal position $Y_i$ of the table top with a loaded weight $W_j$. The couch sag may be a combination of the reference height and the distance in the vertical direction between the table top at the measurement point 351b and the CT isocenter 323. In some embodiments, the couch sag $\Delta B(W_j, Y_i)$ at the measurement point 351b when the table top is at a CT position may be described through Equation (5) below:

$$\Delta B(W_j, Y_i) = D_{CT}^{loaded}(H_o, W_j, Y_i) - H_o, \quad \text{Equation (5)}$$

in which $D_{CT}^{loaded}(H_o, W_j, Y_i)$ refers to a distance between the table top 355 and the CT isocenter 323, $H_o$ refers to a reference height of the table top, $W_j$ refers to a loaded weight, and $Y_i$ refers to a longitudinal position of the table top 355 at the measurement point 351b.

Table B shows standard data describing an exemplary relationship among the couch sag, the longitudinal position at a measurement point 351a corresponding to the RT isocenter when the table top is at an RT position, and a loaded weight. Table B may include couch sags at the measurement point 351a corresponding to the LINAC isocenter for different weights and longitudinal positions, measured by the CBCT technique. At one configuration of the table top when the table top is extended to a position, different longitudinal positions and/or loaded weights may correspond to different RT couch sags. At different configurations of the table top corresponding to different amounts of extension, the measurement point 351a may correspond to different longitudinal positions.

TABLE B

Couch sag at the LINAC isocenter for different weights and longitudinal positions

| | W = 0 | $W_1$ $W_2$ ... $W_j$ | ... $W_N$ |
|---|---|---|---|
| $Y_1 - D_o$ | $D_{CBCT}^{unloaded}(H_o, Y_1 - D_o)$ | | |
| $Y_2 - D_o$ | $D_{CBCT}^{unloaded}(H_o, Y_2 - D_o)$ | | |
| ... | | | |
| $Y_j - D_o$ | | $\Delta A(W_j, Y_i - D_o)$ | |
| ... | | | |
| $Y_N - D_o$ | $D_{CBCT}^{unloaded}(H_o, Y_N - D_o)$ | | |

As shown in Table B, $(Y_N - D_0)$ refers to a longitudinal position at the measurement point 351a corresponding to the RT isocenter when the table top is at an RT position. $Y_N$ refers to the longitudinal position at the measurement point 351b corresponding to the CT isocenter when the table top is at a CT position. $D_o$ refers to a horizontal distance between a CT isocenter and a LINAC isocenter. $W_j$ refers to the weight loaded on a couch. The longitudinal position at the measurement point (e.g., $(Y_1-D_0)$, $(Y_2-D_0)$, $(Y_3-D_0)$, $(Y_N-D_0)$, etc.) and the loaded weight (e.g., $W_1$, $W_2$, $W_3$, $W_N$, etc.) may be any positive number.

$D_{CBCT}^{unloaded}(H_o, Y_N-D_0)$ refers to a distance in the vertical direction between the table top at the measurement point 351a (corresponding to the longitudinal position $Y_N-D_0$) and the LINAC isocenter 333 without a loaded weight, when the reference height is $H_o$.

$\Delta A(W_j, Y_i-D_o)$ refers to a couch sag at the measurement point 351a at a longitudinal position $(Y_i-D_o)$ of the table top with a loaded weight $W_j$. The couch sag may be a combination of the reference height and the distance in the vertical direction between the table top at the measurement point 351a and the RT (e.g., LINAC) isocenter 333. The couch sag $\Delta A(W_j, Y_i-D_o)$ at the measurement point 351a when the table top is at an RT position may be described through Equation (6) below:

$$\Delta A(W_j, Y_i-D_o) = D_{CBCT}^{loaded}(H_o, W_j, Y_i-D_o) - H_o, \quad \text{Equation (6)}$$

in which $D_{CBCT}^{loaded}(H_o, W_j, Y_i-D_o)$ refers to a distance between the table top 355 and the LINAC isocenter 333. $H_o$ refers to a reference height of the table top, $W_j$ refers to a loaded weight, and $Y_i-D_o$ refers to a longitudinal position of the table top 355 at the measurement point 351a.

Figure 13:
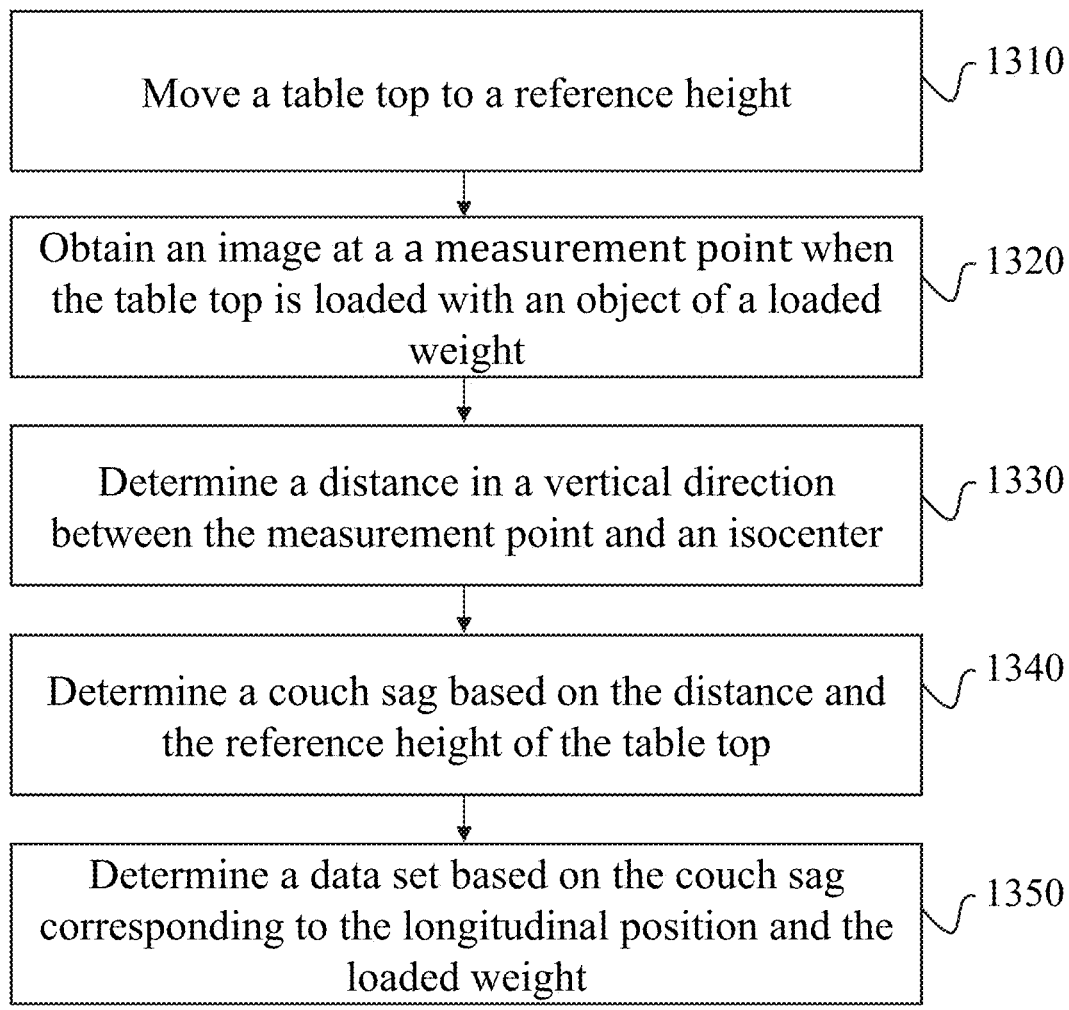
FIG. 13 is a flowchart illustrating an exemplary process for determining a data set of standard data according to some embodiments of the present disclosure.

In some embodiments, the standard data shown in Table A and Table B may be obtained through a process as illustrated in FIG. 13.

Figure 14A:
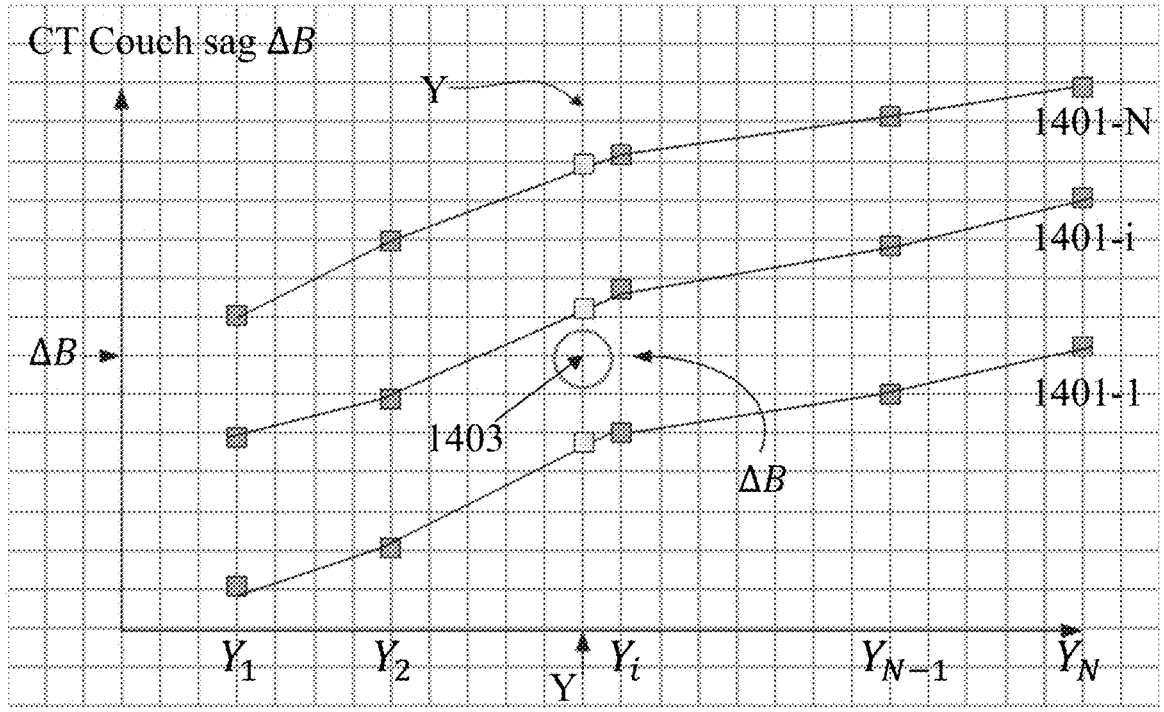
FIGS. 14A and 14B illustrate graphical representations of exemplary standard data according to some embodiments of the present disclosure.
Figure 14B:
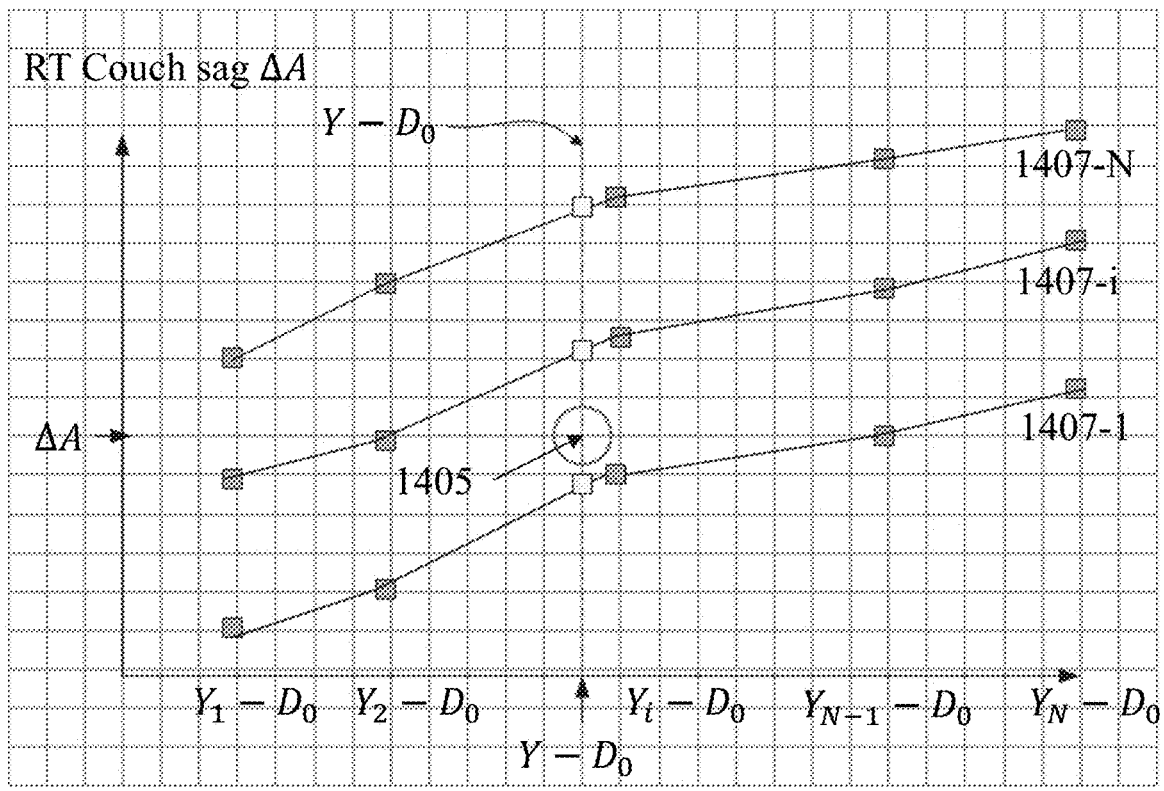

In some embodiments, standard data may be formatted to a graph as shown in FIGS. 14A and 14B. A relationship among a couch sag, a longitudinal position, and a loaded weight shown in the graph may be a straight line, or a polyline, a kinked line, or the like, or a combination thereof.

In some embodiments, standard data may be described by a function. The function may be a real-valued function (e.g., a linear function, a quadratic function, a trigonometric function, etc.), a vector-valued function, a transcendental function, an algebraic function, a continuous function, a non-continuous function, and a monotonic function, or the like, or a combination thereof. For example, the relationship among a couch sag, a longitudinal position, and a loaded weight may be described through Equation (5) and Equation (6).

The pixel data modification module 950 may modify pixel data of an image. For example, the pixel data modification module 950 may process a CT image to generate a representation of a flat couch in the CT image. In some embodiments, for a CT image with a stack of slices, the operation of pixel data modification may be performed slice by slice.

Figure 15A:
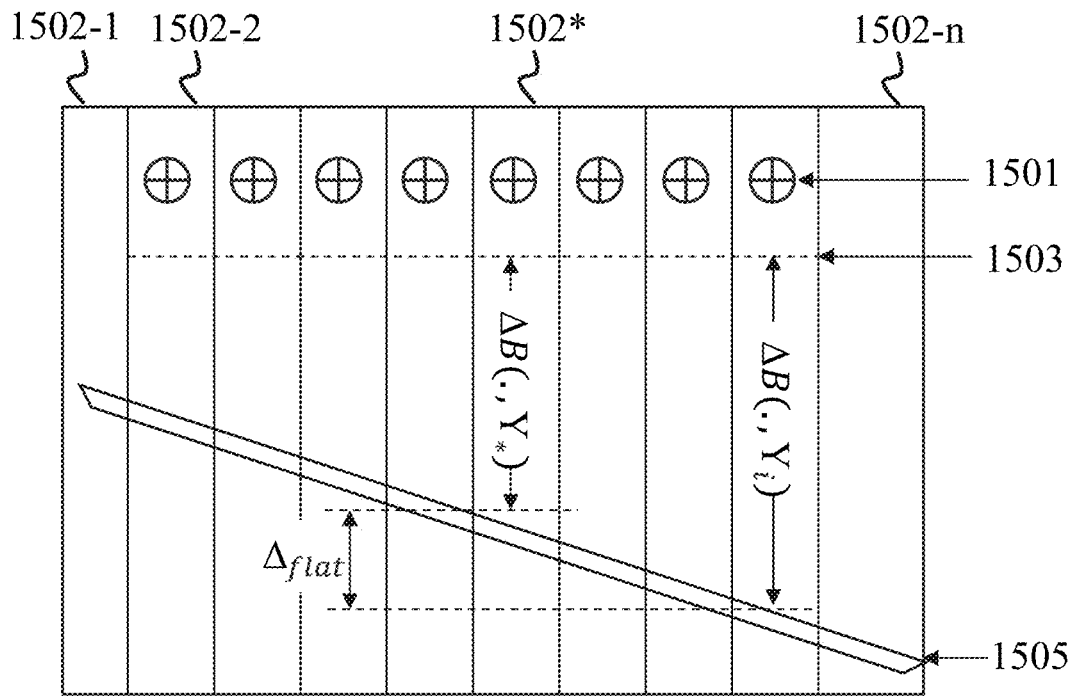
FIG. 15A illustrates a sagittal view of an original CT image according to some embodiments of the present disclosure.

In some embodiments, a couch may be represented as slanted in a CT image as shown in FIG. 15A. The CT image may be modified by moving pixels relating to the table top to a same horizontal level within a slice.

The image registration module 960 may register two or more images. The two or more images may be obtained by the IGRT apparatus 110, generated by the processing engine 140, or retrieved from another source (e.g., the storage 150, a storage, etc.). For instance, a registration may be performed between a planning CT image and a treatment CT image.

The image registration module 960 may perform image registration based on an image registration technique. Exemplary image registration techniques may include an intensity-based technique, a feature-based technique, a transformation model technique, a spatial domain technique, a frequency domain technique, a single-modality technique, a multi-modality technique, an automatic technique, and an interactive technique, or the like, or a combination thereof.

An intensity-based technique may compare intensity patterns in images to be registered based on a correlation metric. A feature-based technique may find correspondence of one or more features in different images to be registered, such as points (e.g., a CT isocenter and a LINAC isocenter, etc.), lines, and contours. For example, the feature-based technique may establish a correspondence between one or more distinct points in a planning CT image and in a treatment CT image.

The control module 970 may provide a control instruction to one or more components of the system 100 including, e.g., the IGRT apparatus 110, etc. For instance, the control module 970 may provide, according to a planning image associated with an original treatment plan, a control instruction to position the table top to a working position of one modality (e.g., the CT device 320, the RT device 330, an LINAC apparatus, etc.) of the IGRT apparatus 110. As another example, the control module 970 may provide, according to information regarding an adjustment of an original treatment plan, a control instruction to move the table top to a working position of the LINAC apparatus such that a desired arrangement is achieved. An example of a desired arrangement is that a target portion of an object (e.g., a tumor of the object, etc.) aligns with the treatment center of the LINAC apparatus (e.g., the LINAC isocenter 333).

FIG. 9B illustrates an exemplary parameter determination module according to some embodiments of the present disclosure. The parameter determination module 930 may include a couch sag determination unit 931 and a treatment isocenter determination unit 933. Components in the parameter determination module 930 may be connected to or communicate with each other and/or other components in the diagnostic and treatment system 100, for example the IGRT apparatus 110, the terminal 130, the display 140, the storage 150, and the processing engine 140 (e.g., the image obtainment module 910, and the data storage module 920, etc.), or the like, or a combination thereof. The parameter determination module 930 may be implemented on the computing device 200 as illustrated in FIG. 2A.

The couch sag determination unit 931 may determine a couch sag. The couch sag may include an RT couch sag in an RT modality (e.g., an RT device, etc.) and/or a CT couch sag in a CT modality (e.g., a CT device, etc.). The RT couch sag may relate to the CT couch sag. Table A and Table B show exemplary relationships between the RT couch sag and the CT couch sag.

In some embodiments, the CT couch sag may be determined based on an image. The image may be a CT image, e.g., a Fan-Beam Computed Tomography image or a Cone-Beam Computed Tomography (CBCT) image. The CT couch sag may be determined based on a reference height (illustrated as dashed line 510) of the table top of a couch and the distance between the CT isocenter 323 to the reference height of the table top of the couch (e.g., the dashed line 510). In some embodiments, the couch sag may be determined based on the coordinates of a loaded table top and the coordinates of an unloaded table top as described in FIG. 11.

Figure 10:
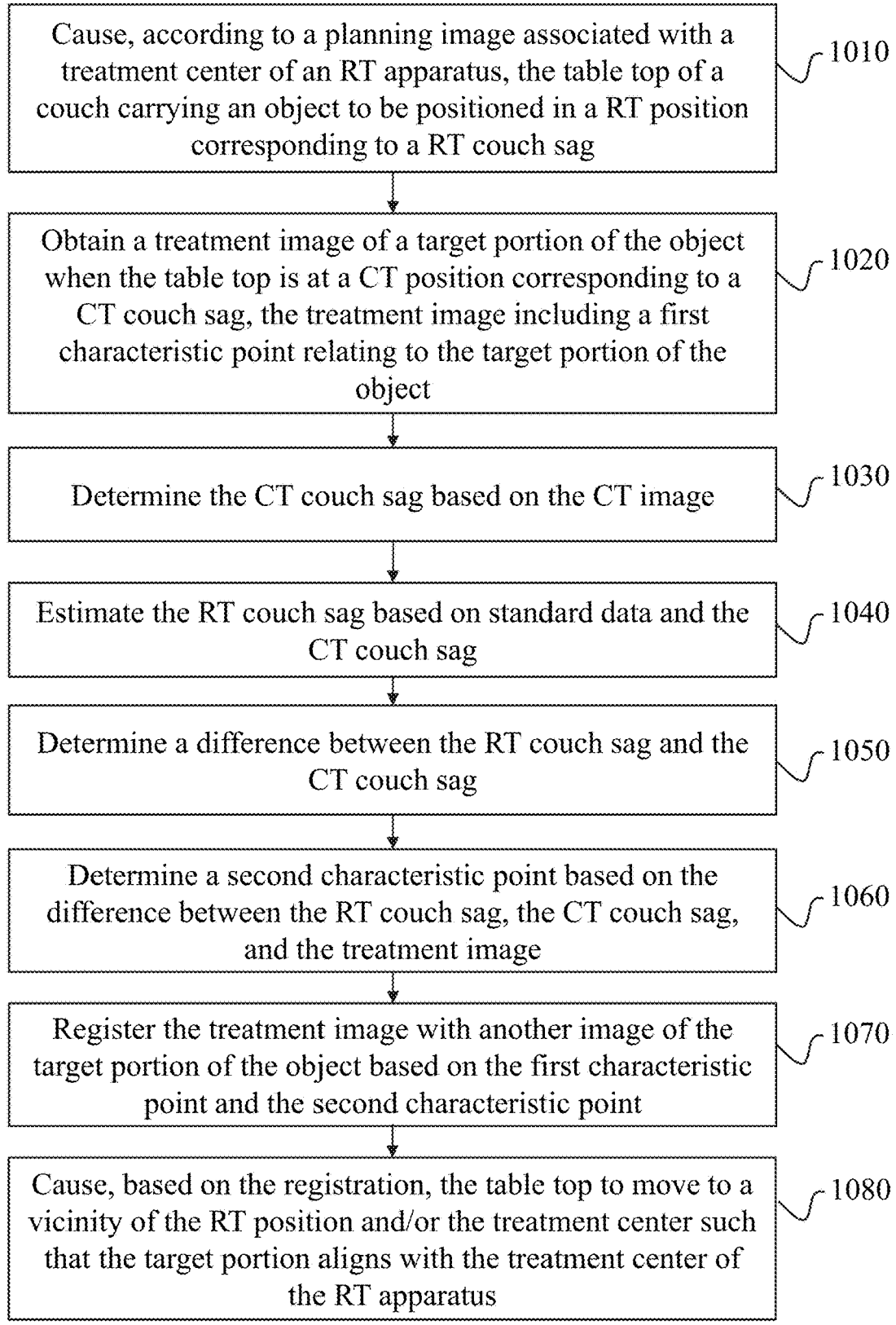
FIG. 10 is a flowchart illustrating an exemplary workflow of a diagnostic and treatment system according to some embodiments of the present disclosure.

In some embodiments, the RT couch sag may be determined based on the CT couch sag and the standard data exemplified in FIG. 10.

In some embodiments, the RT couch sag or the CT couch sag may be determined based on data collected by one or more sensors. For example, a reference height of the table top of a couch and a height of the table top when it is loaded may be determined based on data detected by one or more sensors.

The characteristic point identification unit 933 may determine a second characteristic point in the treatment CT image. Merely by way of example, the second characteristic point in the treatment CT image may correspond to an internal anatomical point, which in turn may correspond to a tumor. In some embodiments, the internal anatomical point 801 may be located underneath a CT isocenter 323 by a distance of ($\Delta B - \Delta A$) as shown in FIG. 8 without considering the movement of the couch 350 in the Z direction (e.g., $\Delta h$).

It should be noted that the descriptions above in relation to the parameter determination module 930 is provided for the purposes of illustration, and not intended to limit the scope of the present disclosure. For persons having ordinary skills in the art, various variations and modifications may be conducted under the guidance of the present disclosure. However, those variations and modifications do not depart from the scope of the present disclosure. For example, the parameter determination module 930 may include a position parameter determination unit (not shown in figures). The position parameter determination unit may determine position parameters for positioning a patient. As another example, each of components of the parameter determination module 930 may include a storage.

It should be noted that the descriptions above in relation to the processing engine 140 and the parameter determination module 930 are provided for the purposes of illustration, and not intended to limit the scope of the present disclosure. For persons having ordinary skills in the art, various variations and modifications may be conducted under the guidance of the present disclosure. However, those variations and modifications do not depart from the scope of the present disclosure. For example, each of components of the processing engine 140 may include a storage. As another example, standard data generation module may not be needed, and the standard data may be generated in other device and storage in the data storage module 920.

FIG. 10 is a flowchart illustrating an exemplary workflow of a diagnostic and treatment system in accordance with some embodiments of the present disclosure. Process 1000 may be performed by the diagnostic and treatment system 100. One or more operations of process 100 may be performed by the processing engine 140. The processing engine 140 may be implemented on computing device 200 as illustrated in FIG. 2A.

In 1010, an initial setup may be performed. In the initial setup, an object (e.g., a patient, etc.) may be positioned on the table top 355 of the couch 350 at an RT position corresponding to an RT couch sag.

In the initial setup, the position of an object on the table top 355 of the couch 350 and/or the couch 350 may be so that one or more lasers of the RT device 330 may align with one or more surface markers of the object on the table top 355. The one or more lasers may correspond to a LINAC isocenter of the RT device 330. The one or more surface markers may correspond to an internal anatomical point (e.g., a point of a tumor, etc.). By the initial setup, the LINAC isocenter of the RT device 330 may align with the internal anatomical point. In some embodiments, the couch sag at the first measurement point 351a may be $\Delta A$ (but not actually measured during initial setup procedure) after the positioning of the object, as shown in FIG. 5. In some embodiments, the initial setup may base on a planning CT image. The internal anatomical point may correspond to a first characteristic point of the planning CT image determined by a physicist or determined by a processor of the diagnostic and treatment system 100. Herein, the first characteristic point in the planning CT image may substantially align with the LINAC isocenter or be spaced by a distance from the LINAC isocenter. That is, the relationship between the first characteristic point and the LINAC isocenter is known.

In 1020, a treatment image of a target portion of the object may be obtained when the table top is at a CT position corresponding to a CT couch sag. The treatment image may be a treatment CT image. The treatment image may be obtained by the image acquisition module 910. For example, the treatment image may be obtained by the CT device 320. The imaging plane (e.g., a side view of the imaging plane may be line 321) of the CT device 320 may be perpendicular to a longitudinal axis passing through the LINAC isocenter 333 and the CT isocenter 323.

For example, after the initial setup in the RT device 330 at an RT position, the table top 355 may be moved to at a CT position where a CT scan may be performed by the CT device 320. The couch may sag by an amount of $\Delta B$ at the measurement point 351b.

Figure 11:
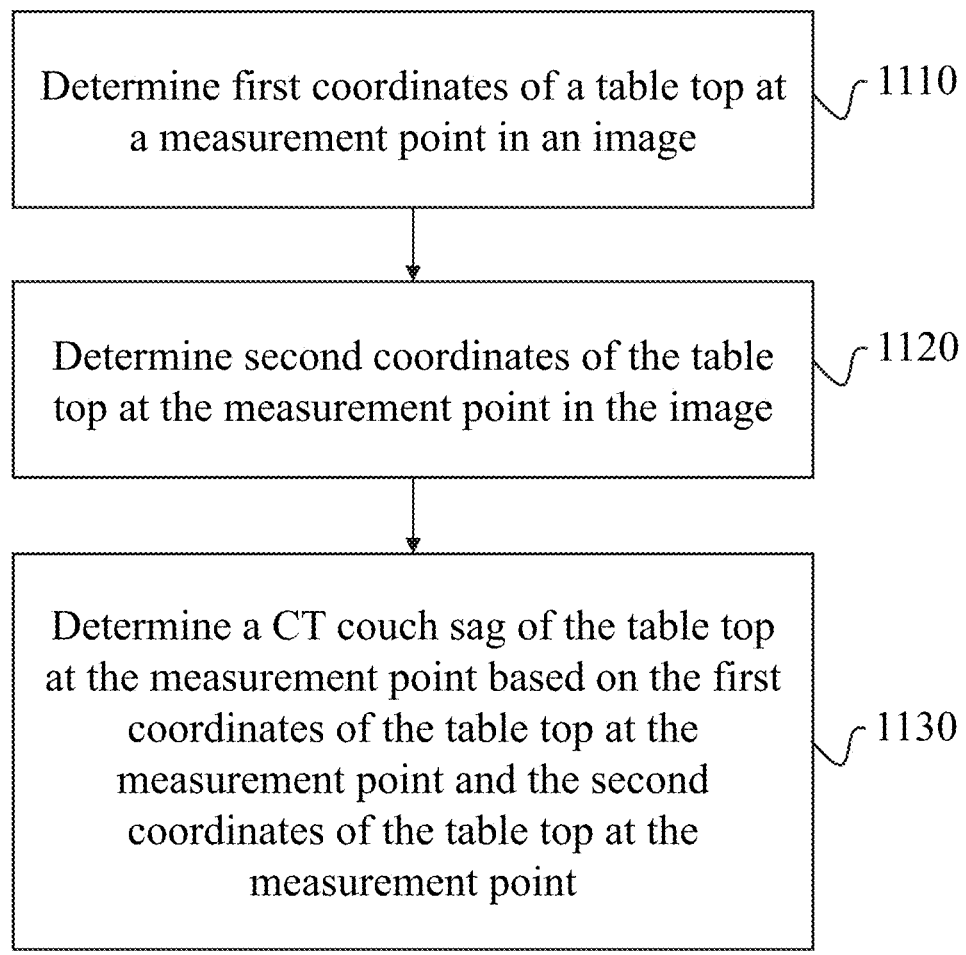
FIG. 11 is a flowchart illustrating an exemplary process for determining a couch sag according to some embodiments of the present disclosure.

In 1030, a CT couch sag may be determined based on the CT image. For example, the CT image may be a treatment CT image. The determination may be performed by the parameter determination module 930. For instance, the determination may be performed by couch sag determination unit 931. The CT couch sag may be determined based on the coordinates of the unloaded table top at a measurement point and the coordinates of the loaded table top at the measurement point as illustrated in FIG. 11.

In some embodiments, after a treatment CT image of an object at a CT position is obtained, the table top 355 carrying the object may be retracted to an RT position for treatment. The couch sag at the RT position may equal to the couch sag as described in the initial setup process.

Figure 12:
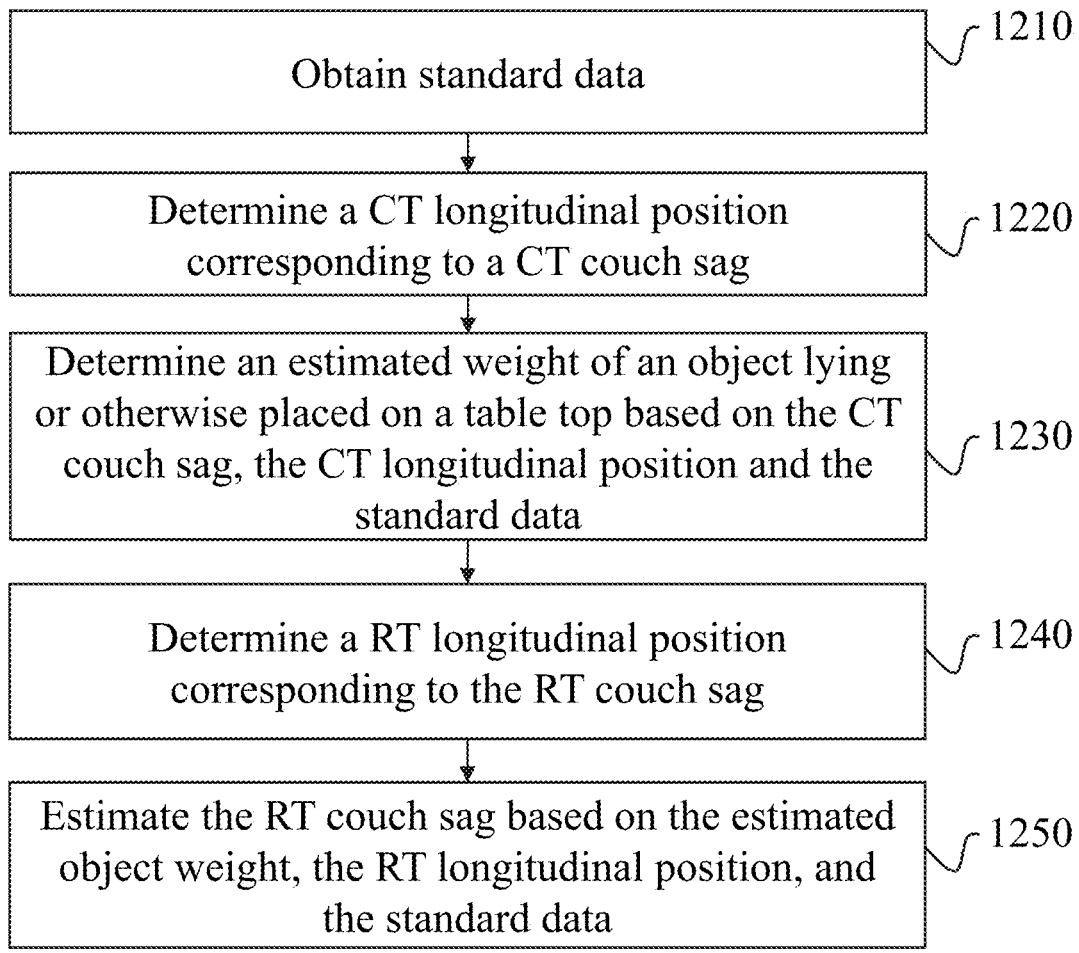
FIG. 12 is a flowchart illustrating an exemplary process for determining a couch sag according to some embodiments of the present disclosure.

In 1040, the RT couch sag may be estimated based on standard data and the CT couch sag. The estimation may be performed by the parameter determination module 930. For instance, the estimation may be performed by couch sag determination unit 931. The estimation of the RT couch sag may be based on the weight (e.g., a patient weight, etc.) loaded on the table top 355. The weight may be estimated, measured, or retrieved from a source (e.g., the records of a patient). Process 1200 illustrated in FIG. 12 is an exemplary process for estimating an RT couch sag.

In 1050, a difference between the RT couch sag and the CT couch sag may be determined. The determination may be performed by the parameter determination module 930. For instance, the determination of the difference between the RT couch sag and the CT couch sag may be performed by the characteristic point identification unit 933. In some embodiments, the difference between the CT couch sag and the RT couch sag may be denoted by (AB−ΔA).

In 1060, a second characteristic point may be determined based on the difference between the RT couch sag, the CT couch sag, and the treatment image (e.g., the treatment CT image, etc.). The determination of the second characteristic point may be performed by the parameter determination module 930. For instance, the determination of the second characteristic point may be performed by the second characteristic point identification unit 933.

Descriptions regarding a relationship of the second characteristic point, a CT scan isocenter, and a LINAC isocenter may be found elsewhere in the present disclosure. See, for example, FIG. 8 and the description thereof.

In 1070, two different images of the object may be registered. The registration may be performed by the image registration module 960.

In some embodiments, a registration may be performed between a planning CT image and a treatment CT image. The registration may include one or more of the following operations. The second characteristic point in the treatment CT image may be aligned with a first character point in the planning CT image. As used herein, a planning CT image may be a CT image generated by a planning CT scan and marked with a treatment plan. For instance, in a planning CT image, areas that need treatment may be identified, and the areas where radiation needs to be limited or avoided may be outlined by a user including, for example, a physician and/or radiotherapy specialist. In some embodiments, the user may mark a CT image via a user interface implemented on or connected to the computing device 200 and/or the mobile device 200B. The first character point (e.g., a point representing a tumor in CT image, etc.) may be a point determined in the treatment plan. The outline of the object in the treatment CT image and the outline of the object in the planning CT image may be compared. If the object outline in the treatment CT image corresponds or essentially corresponds with the object outline in the planning CT image, the registration may end and a movement of the table top 355 of the couch 350 or the RT device 330 may be determined. If the object outline in the treatment CT image does not correspond or essentially correspond with the object outline in the planning CT image, position adjustment data may be determined through a position adjustment algorithm. Descriptions regarding registration may be found elsewhere in the present disclosure. See, for example, FIG. 9A and the description thereof.

In some embodiments, the table top 355 of the couch 350 and/or the couch 350 may be moved to a vicinity of the initial setup position determined in the initial setup process based on the registration result. For example, the diagnostic and treatment system 100 may move the table top 355 of the couch 350 and/or the couch 350 to a vicinity of an RT position based on the registration.

In some embodiments, the treatment center of the RT device 330 (e.g., the LINAC isocenter 333) may be adjusted based on the registration.

In some embodiments, before 1070, a treatment CT image may be modified to generate the representation of a flat table top in the treatment CT image. Descriptions regarding generation the representation of the flat couch may be found elsewhere in the present disclosure. See, for example, FIG. 15A and FIG. 15B and the description thereof.

In 1080, based on the registration, the table top 355 may be moved to a vicinity of the RT position, or the treatment center may be adjusted, or both may be performed, such that the target portion of the object aligns with the treatment center of the RT device 330. In some embodiments, the movement of the table top 355 and/or the adjustment of the treatment center of the RT device 330 may be based on a control instruction provided by the control module 970.

It should be noted that process 1000 described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart from the scope of the present disclosure. For instance, an artifact removal operation may be performed with respect to a treatment CT image and/or a planning CT image before the registration of the treatment CT image and the planning CT image. Similar modifications should fall within the scope of the present disclosure.

FIG. 11 is a flowchart illustrating an exemplary process for determining a couch sag in accordance with some embodiments of the present disclosure. Process 1100 may be performed by the couch sag determination unit 931. The couch sag determination unit 931 may be implemented on computing device 200 as illustrated in FIG. 2A.

In 1110, the first coordinates of a table top at a measurement point may be determined in an image. The table top may be loaded with an object. For example, the measurement point may be the measurement point 351b corresponding to the CT isocenter 323 as shown in FIG. 8. The weight of the object may be any value. The image may be a CT image. For example, the image may be a CT image obtained by the CT device 320.

In 1120, the second coordinates of the table top at the measurement point may be determined in the image. The second coordinates of the table top may be coordinates of the table top in an ideal condition without a couch sag (e.g., a couch sag caused by a loaded weight, couch sag caused by the weight of the couch).

In some embodiments, the second coordinates be determined based on one or more of the following operations. The coordinates of a CT machine isocenter in the image may be determined. The CT machine isocenter may correspond to a center (e.g., a geometrical center, a CT scanning center) of the image. For example, the coordinates of the CT machine isocenter may be equal to the coordinates of the CT scanning center. As another example, the coordinates of the CT machine isocenter may be determined based on the coordinates of the CT scanning center and a displacement of the CT machine isocenter and the CT scanning center. The displacement may be set or selected by a user of the diagnostic and treatment system 100.

Information regarding the table top position may be obtained for, e.g., a prior measurement. For instance, the information regarding the table top position may be retrieved from a storage (e.g., the storage 150, the data storage module 920, etc.). The second coordinates of the table top at the measurement point may be determined based on the coordinates of the CT machine isocenter and the table top position. The table top position may not be the actual position of the table top because of the couch sag. The table top position is an ideal position of the table top position without couch sag. The second coordinates of the table top at the measurement point may be ideal coordinates of the table top at the measurement point without couch sag.

In some embodiments, the second coordinates of the table top at the measurement point may be stored in a storage (e.g., the storage 150, the data storage module 920, etc.). The second coordinates of the table top at the measurement point may be retrieved from the storage for future use.

In 1130, a CT couch sag of the table top at the measurement point may be determined based on the first coordinates of the table top at the measurement point and the second coordinates of the table top at the measurement point.

In some embodiments, an image may be a CT image. The CT couch sag may be described through Equation (7) below:

$$\Delta B = Z_{actual} - Z_{ideal}, \quad (7)$$

in which $Z_{actual}$ refers to first coordinates of the table top at a measurement point with a couch sag, and $Z_{ideal}$ refers to second coordinates of the table top at the measurement point without a couch sag.

FIG. 12 is a flowchart illustrating an exemplary process for determining a couch sag in accordance with some embodiments of the present disclosure. Process 1200 may be performed by the couch sag determination unit 931. The couch sag determination unit 931 may be implemented on the computing device 200 as illustrated in FIG. 2A. Process 1200 is an exemplary process for performing 1040 as described in FIG. 10 for estimating an RT couch sag based on standard data and a CT couch sag. In some embodiments, the couch sag may be an RT couch sag at an RT position. The CT longitudinal position and the CT couch sag may correspond to a second measurement point (e.g., the measurement 351*b*). The RT longitudinal position and the RT couch sag may correspond to a first measurement point (e.g., the measurement point 351*a*).

In 1210, standard data may be obtained. The standard data may include a plurality of standard data set. A standard data set may include a first standard parameter and a second standard parameter. The first standard parameter may relate to the table top of a couch when the table top is located at a working position of a first device, or referred to as a first modality unit (e.g., an RT device, etc.). The second standard parameter may relate to the table top of the couch when the table top is located at a working position of a CT device, or referred to as a CT modality unit.

In some embodiments, the first standard parameter may be a predetermined parameter corresponding to RT device 330. For example, the first standard parameter may be a value from Table B or from a graph as shown in FIG. 14B. The second standard parameter may be a predetermined parameter corresponding to the CT device 320. For example, the second standard parameter may be a value from Table A as shown in FIG. 9A or from a graph as shown in FIG. 14A.

In 1220, a CT longitudinal position corresponding to a CT couch sag (e.g., AB as shown in FIG. 14A) may be determined. The CT couch sag may be measured at the CT longitudinal position when an object lies or is otherwise placed on the table top of the couch. In some embodiments, the CT longitudinal position may be determined based on a measurement point (e.g., 351*b* illustrated in FIGS. 6-8, 16C, and 16D) corresponding to the isocenter of the CT device when the table top is at a CT position. The longitudinal position may be Y. For example, the longitudinal position may be Y corresponding to ΔB as shown in FIG. 14A.

In 1230, the weight W of the object lying or otherwise placed on the table top of the couch may be estimated based on the CT couch sag, the CT longitudinal position, and the standard data.

The weight W may be estimated based on information of point 1403 as shown in FIG. 14A. The coordinates of point 1403 may be (Y, ΔB). In some embodiments, the weight W may be obtained by, for example, a record of the object, measurement by a scale, etc.

In 1240, an RT longitudinal position corresponding to the RT couch sag may be determined. In some embodiments, the RT longitudinal position may be determined based on a measurement point (e.g., 351*a* illustrated in FIGS. 5, 8, 16B, and 16E) corresponding to the isocenter of the RT device when the table top is at an RT position. The RT longitudinal position may be (Y-D$_o$) as shown in FIG. 8.

In 1250, the RT couch sag may be estimated based on the estimated object weight, the RT longitudinal position, and the standard data. Based on the estimated object weight W and the T longitudinal position (Y-D$_o$), the RT couch sag ΔA may be determined as shown in FIG. 14B.

FIG. 13 is a flowchart illustrating an exemplary process for determining a data set of the standard data in accordance with some embodiments of the present disclosure. The standard data may include a plurality of data sets. A data set may include the values of or information relating to a longitudinal position (corresponding to an amount of extension of the table top), a loaded weight, and a corresponding couch sag. In some embodiments, a standard data set may include a first standard parameter and a second standard parameter. The first standard parameter may include a relationship between a couch sag of the table top, and an amount of extension of the table top when the table top is at an RT position. The second standard parameter may include a relationship between a couch sag of the table top and an amount of extension of the table top when the table top is at a CT position. Process 1300 may be performed by the standard data generation module 940. The standard data generation module 940 may be implemented on computing device 200 as illustrated in FIG. 2A. The longitudinal position may correspond to a measurement point of the table top.

In 1310, a table top may be moved to a reference height. The reference height may be H$_k$. The value of H$_k$ may be a random value, an empirical value, or a value that meets a specific condition. In some embodiments, a reference height may be a fixed height $H_0$.

In 1320, an image may be obtained at a measurement point when the table top is loaded with an object of a loaded weight. The image may be a CT image, a CBCT image, an MR image, or the like.

In some embodiments, the longitudinal position of the table top at the measurement point may be $Y_i$ at a CT position. The loaded weight may be $W_j$. In some embodiments, the image may be a CT image obtained by a CT device.

In some embodiments, the longitudinal position of the table top the measurement point may be $(Y_i-D_0)$ after the couch is moved from a CT position to an RT position.

In 1330, a distance in a vertical direction between the table top at the measurement point and an isocenter may be determined. The isocenter may be the CT isocenter 323 or the LINAC isocenter 333. The distance may be denoted as $D(H_k, W_j, Y_i)$. The distance may be obtained by way of a measurement using a sensor, a calculation based on a reported parameter (e.g., a table top position, etc.), or the like.

In some embodiments, an image may be a CT image obtained at a CT position. When the table top is loaded with an object of weight $W_j$, the distance between the table top at the measurement point and the CT isocenter 323 may be denoted as $D_{CT}^{loaded}(H_k, W_j, Y_i)$. When the table top is not loaded (i.e. a loaded weight is zero), the distance may be denoted as $D_{CT}^{unloaded}(H_k, W_j, Y_i)$. In such a situation, $W_j=0$, the distance may be denoted as $D_{CT}^{unloaded}(H_k, Y_i)$. See, for example, Table A and the description thereof.

In some embodiments, an image may be a CBCT image obtained at an RT position. With a loaded weight $W_j$, the distance in the vertical direction between the table top at the measurement point and the CBCT isocenter may be denoted as $D_{CBCT}^{unloaded}(H_k, W_j, Y_i)$. When the table top is not loaded (i.e., a loaded weight is zero.), the distance may be denoted as $D_{CBCT}^{unloaded}(H_k, W_j, Y_i)$. In suc ha situation, $W_j=0$, the distance may be denoted as $D_{CBCT}^{unloaded}(H_k, Y_i)$.

In 1340, a couch sag may be determined based on the distance and the reference height of the table top. The couch sag may be a combination or sum of the distance and the reference height.

In some embodiments, a couch sag may be a CT couch sag corresponding to a CT image. The CT couch sag $\Delta B(W_j, Y_i)$ may be described through Equation (8) below:

$$\Delta B(W_j, Y_i) = D_{CT}^{loaded}(H_k, W_j, Y_i) - H_k.\qquad \text{Equation (8)}$$

In some embodiments, a couch sag may be an RT couch sag corresponding to an RT position obtained by an imaging device, e.g., a CBCT device. The RT couch sag $\Delta A(W_j, Y_i-D_o)$ may be described through Equation (9) below:

$$\Delta A(W_j, Y_i-D_o) = D_{CBCT}^{loaded}(H_k, W_j, Y_i-D_o) - H_k.\qquad \text{Equation (9)}$$

In 1350, a data set may be determined based on the couch sag corresponding to the longitudinal position and the loaded weight.

In some embodiments, an image may be obtained at a CT position. Correspondingly, a data set corresponding to the CT position may be described through Equation (10) below:

$$\text{Set } B_{j,i,k} = \{\Delta B(W_j, Y_i), H_k, Y_i\}\qquad \text{Equation (10)}$$

In some embodiments, an image may be obtained at an RT position. Correspondingly, a data set corresponding to the RT position may be described through Equation (11) below:

$$\text{Set } A_{j,i,k} = \{\Delta A(W_j, Y_i-D_o), H_k, Y_i-D_o\}.\qquad \text{Equation (11)}$$

In some embodiments, a plurality of data sets may be obtained by measurements with different loaded weights and longitudinal positions at various CT positions or various RT positions. For example, the loaded weight may be 0, 50 kg, 100 kg, . . . , 150 kg, etc. For example, the longitudinal position at the CT position may be $Y_a$ to $Y_b$ and the corresponding longitudinal position at the RT position (e.g., couch 350 retracted form a CT position to an RT position) may be $(Y_a-D_0)$ to $(Y_b-D_o)$.

In some embodiments, it is shown in the example 1 hereinafter that, a couch sag may be independent of the reference height of the table top at which the measurements are conducted, and thus the data of couch sag acquired at the fixed couch height $H_o$ may be used for various reference height of the table top.

In some embodiments, a couch sag at a CT position and a corresponding couch sag at an RT position may be determined based on Equations (12) and (13) below:

$$\Delta B(W, Y_i) = D_{CT}^{loaded}(H_o, W, Y_i) - H_o,\qquad \text{Equation (12)}$$
$$= D_{CT}^{loaded}(H, W, Y_i) - H$$

and $$\Delta A(W, Y_i - D_o) = D_{CBCT}^{loaded}(H_o, W, Y_i - D_o) - H_o.\qquad \text{Equation (13)}$$
$$= D_{CBCT}^{loaded}(H, W, Y_i - D_o) - H$$

FIGS. 14A and 14B illustrate graphical representations of exemplary standard data according to some embodiments of the present disclosure. The standard data may include a plurality of data sets. A data set may include the values of a longitudinal position, a loaded weight, and a corresponding couch sag. Standard data as shown in FIGS. 14A and 14B may be used to estimate an RT couch sag (e.g., an RT couch sag, etc.) based on a CT couch sag.

In both FIGS. 14A and 14B, the horizontal axis may refer to a longitudinal position, and the vertical axis may refer to a couch sag. The coordinates of point 1403 may be (AB, Y) and the coordinates of point 1405 may be $(\Delta A, Y-D_o)$. FIG. 14A may include second standard parameters corresponding to a CT device. Line 1401 (e.g., line 1401-1, 1401-i, and 1401-N, etc.) may correspond to standard data sets obtained at different loaded weights (e.g., $W_1$, $W_i$, and $W_N$, etc.) and longitudinal positions (e.g., $Y_1$, $Y_i$, and $Y_N$, etc.). The longitudinal positions may correspond to the measurement point associated with the isocenter of the CT device (e.g., 351b as illustrated in FIGS. 6-8, 16C, and 16D).

FIG. 14B may include first standard parameters corresponding to an RT device. Line 1407 (e.g., line 1407-1, 1407-i, and 1407-N, etc.) may correspond to data sets obtained at different loaded weights (e.g., $W_1$, $W_i$, and $W_N$, etc.) and longitudinal positions (e.g., $(Y_1-D_0)$, $(Y_i-D_0)$, and $(Y_N-D_0)$, etc.). The longitudinal positions may correspond to the measurement point associated with the isocenter of the RT device (e.g., 351a as illustrated in FIGS. 5, 8, 16B, and 16E).

It should be noted that graphical representations of the standard data described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart from the scope of the present disclosure. In some embodiments, a difference of $\Delta B$ and $\Delta A$ (e.g., $\Delta B-\Delta A$) may be used as a horizontal axis and a difference of ΔB and ΔA may be determined based on the standard data and ΔB. Similar modifications fall within the scope of the present disclosure.

Figure 15B:
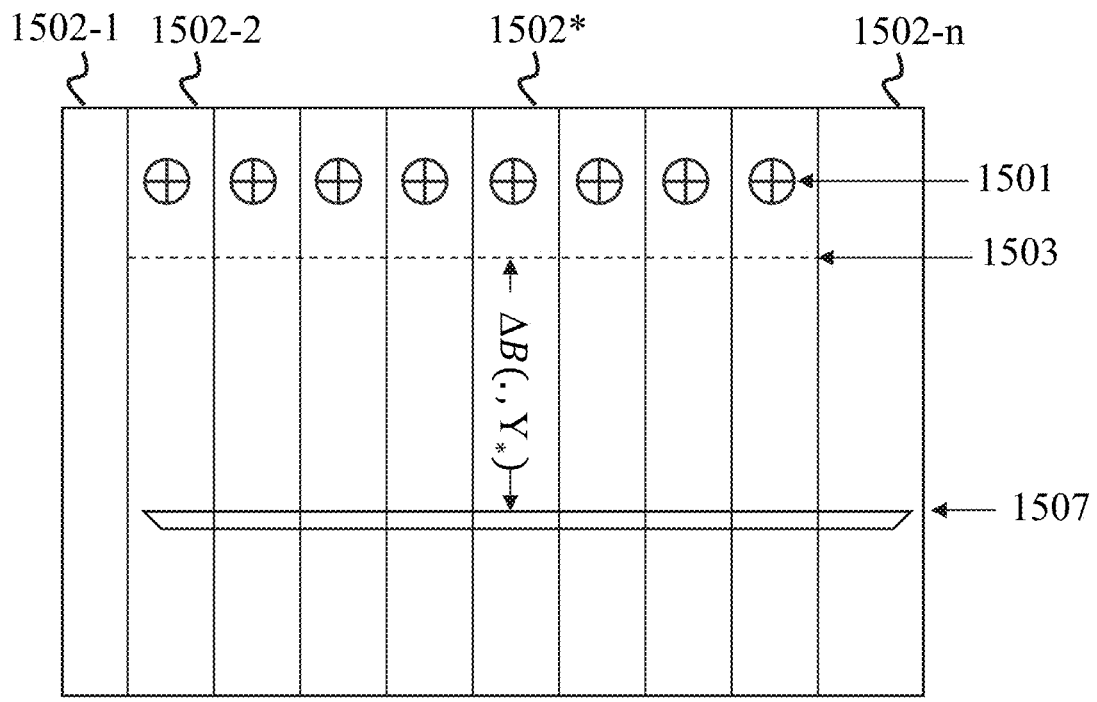
FIG. 15B illustrates a sagittal view of a CT image after pixel modification according to some embodiments of the present disclosure.

FIG. 15A illustrates a sagittal view of an original CT image according to some embodiments of the present disclosure. FIG. 15B illustrates a sagittal view of a CT image after pixel data modification according to some embodiments of the present disclosure. The pixel data modification of a CT image may be performed by a pixel data modification module 950. The pixel data modification module 950 may be implemented on computing device 200 as illustrated in FIG. 2A. In some embodiments, the CT image may be displayed on the display 255 of the mobile device 200B as described in FIG. 2B.

The CT image as shown in FIG. 15A and FIG. 15B may include a plurality of slices 1502 (e.g., 1502-1, 1502-2, 1502*, and 1502-n, etc.) The reference height of the couch is H (i.e., the height of the table top at its retracted as shown in FIG. 16A position is H). The CT image may be obtained when the reference height is H. Each of slices 1502 may correspond to a longitudinal position Y (e.g., $Y_1$, $Y^*$, $Y_n$, etc.) of the table top 355 of the couch 350 measured from a reference point, e.g., the origin of the table top 355. For example, slice 1502-1 may correspond to longitudinal position $Y_1$. Line 1501 may represent a plane where a CT isocenter is located. Line 1503 may represent the level of the table top at a longitudinal position $Y=Y^*$ and the reference height H. Quadrilateral 1505 may be a representation of a slanted table top as shown in FIG. 15A, and quadrilateral 1507 may be a representation of a flat table top generated by way of modification of quadrilateral 1505. Description regarding pixel data modification may be found in, for example, Chinese Patent Application No. 201611258746.8 entitled "System and method for couch calibration and couch apparatus" and Chinese Patent Application No. 201611262204.8 entitled "System and method for image reconstruction," both filed on Dec. 30, 2016, the contents of which are hereby incorporated by reference.

A planning CT image may be obtained with a flat (or horizontal) couch. To achieve better accuracy in registration, a treatment CT volume pixel data may be modified to represent a flat couch. In a pixel data modification operation, the table top in a slice may be determined and pixel data of the table top in every slice may be moved up or down by an amount so that the representation of a flat table top may be generated. For brevity, the representation of an item in an image may be referred to as that item in the image. For instance, the representation of the table top in an image may be referred to as the table top in the image. Through the modification, the table top in the slice may be at a fixed distance from the CT isocenter in the slice.

In some embodiments, the pixel data modification operation may include one or more of the following. A fixed distance from the table top to the CT isocenter may be identified. The pixels in a slice may be moved so that the table top in that slice is located at the same distance from the CT isocenter. For example, the fixed distance from the table top to the CT isocenter may be identified in a slice of a longitudinal position $Y=Y^*$ and a reference height H. In another slice where $Y \neq Y^*$, a table top may be identified and the pixels corresponding to the table top may be moved up or down with a couch sag difference. The couch sag difference $\Delta_{flat}(Y)$ may be described using Equation (18):

$$\Delta_{flat}(z) = \Delta B(., Y) - \Delta B(., Y^*), \quad (18)$$

wherein $\Delta B(., Y)$ refers to a couch sag in a slice obtained at a longitudinal position Y of the table top at the measurement point associated with the CT isocenter (e.g., 351b in FIG. 6), and $\Delta B(., Y^*)$ refers to a couch sag in a slice obtained at a longitudinal position $Y^*$.

In some embodiments, if $\Delta_{flat}(Y)>0$, the pixels relating to the table top may be moved up by $|\Delta_{flat}(Y)|$. If $\Delta_{flat}(Y)<0$, the pixels relating to the table top may be moved down by $|\Delta_{flat}(Y)|$.

It should be noted that pixel data modification described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart from the scope of the present disclosure. In some embodiments, an artifact removal operation may be needed after the pixel data modification. Similar modifications should fall within the scope of the present disclosure.

EXAMPLES

The following examples are provided for illustration purposes, and not intended to limit the scope of the present disclosure.

Example 1

For an object of weight W and the couch longitudinal position $Y_i$, CT images were acquired at $Y_i$, and CBCT images were acquired at $(Y_i-D_o)$, as described elsewhere in the present disclosure. See, for example, FIG. 13 and the description thereof. Measurements of the distance in the vertical direction of the measurement point from the isocenter (e.g., the CT isocenter or CBCT isocenter) with or without loaded object, were conducted as described elsewhere in the present disclosure. See, for example, FIG. 13 and the description thereof. These measurements were conducted at different reference heights of the table top, $H_1$, $H_2$ etc. When it was found the relationship shown in Equations (14)-(17), the couch sag was considered independent of the reference height of the table top.

$$D_{CT}^{unloaded}(H_o, Y_i) - D_{CT}^{unloaded}(H_j, Y_i) = H_j - H_o, \quad \text{Equation (14)}$$

$$D_{CT}^{loaded}(H_o, W, Y_i) - D_{CT}^{loaded}(H_j, W, Y_i) = H_j - H_o, \quad \text{Equation (15)}$$

$$D_{CBCT}^{unloaded}(H_o, Y_i - D_o) - D_{CBCT}^{unloaded}(H_j, Y_i - D_o) = H_j - H_o, \quad \text{Equation (16)}$$

and $$D_{CBCT}^{loaded}(H_o, W, Y_i - D_o) - D_{CBCT}^{unloaded}(H_j, W, Y_i - D_o) = H_j - H_o, \quad \text{Equation (17)}$$

Example 2

An RT couch sag ΔA may be determined based on a CT couch sag ΔB, a longitudinal position Y, and standard data as shown in FIGS. 14A and 14B. The determination of the RT couch sag may be performed by the processor 210 as shown in FIG. 2A. The standard data as shown in FIGS. 14A and 14B may be stored in the storage 220 as shown in FIG. 2A.

The processor 210 may determine a point 1403 as shown in FIG. 14 based on the CT couch sag ΔB at a measurement point at the longitudinal position Y at a CT position. The CT couch sag ΔB may be obtained from a CT image of an object taken at the CT position. The weight of the object may be W.

Based on the standard data as shown in FIG. 14A, the weight W may be estimated. In some embodiments, the weigh W may be obtained by one or more other ways. For instance, the weight W may obtained from a record regarding the object.

Based on the longitudinal position Y at a CT position a longitudinal position at an RT position may be determined as $Y-D_o$. Then a point 1405 may be identified in FIG. 14B based on the weight W and a longitudinal position $Y-D_o$ at the RT position. Based on the coordinates of point 1405 in FIG. 14B, a couch sag at the RT position may be determined as ΔA.

Example 3

FIGS. 16A-16E illustrate different configurations of the table top of a couch according to some embodiments of the present disclosure.

FIG. 16A illustrates the table top at its retracted configuration according to some embodiments of the present disclosure. As used herein, the retracted configuration of the table top may refer to the condition when the table top is fully retracted to its resting position.

Figure 16D:
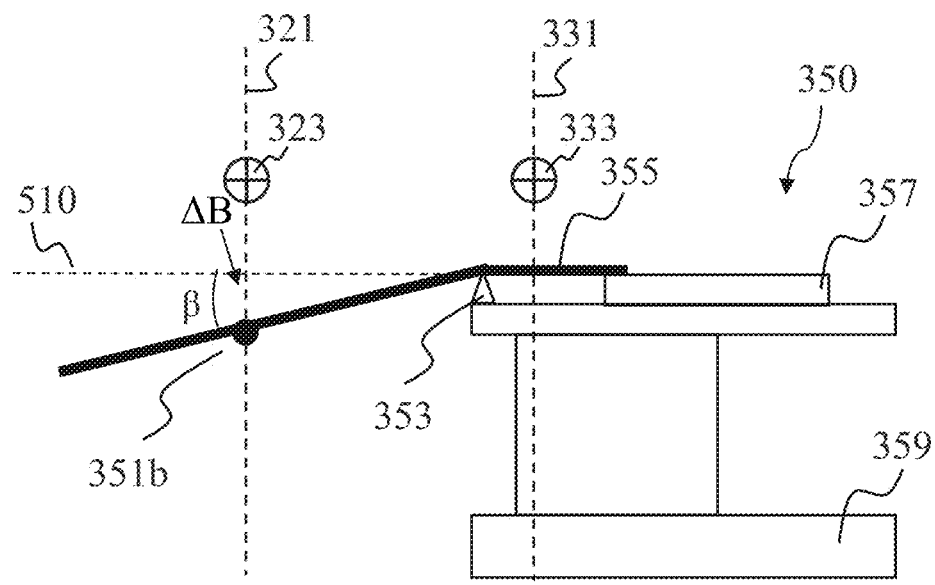
Figure 16E:
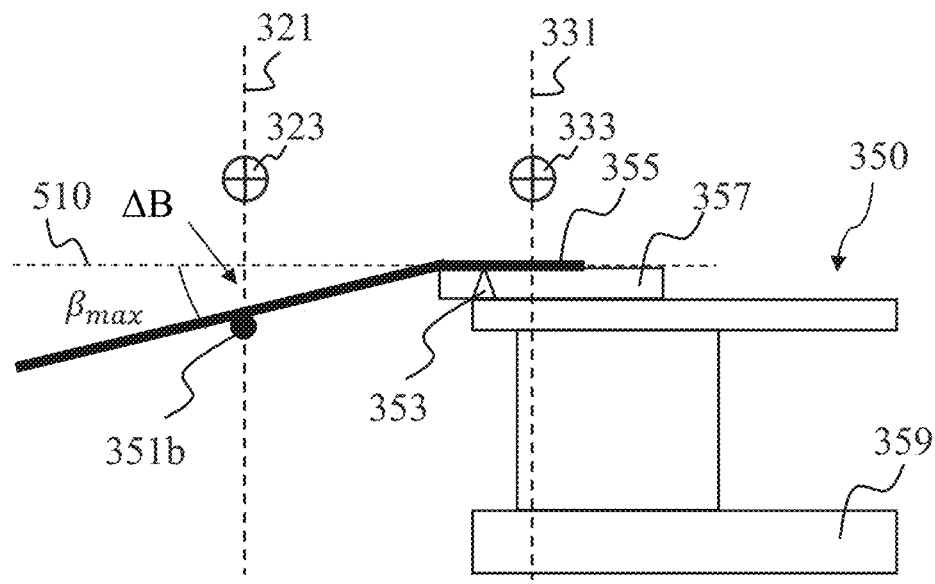
FIG. 16E illustrates the table top at its extended configuration according to some embodiments of the present disclosure.

FIG. 16B, FIGS. 16C, and 16D illustrate partially extended configurations of the table top according to some embodiments of the present disclosure. As used herein, a partially extended configuration of the table top may refer to the condition of the table top when the table top is partially extended between its retracted configuration and its extended configuration.

FIG. 16E illustrates the table top at its extended configuration according to some embodiments of the present disclosure. As used herein, the extended configuration of the table top may refer to the condition when the table top is fully extended.

In an initial setup of an IGRT procedure, the couch 350 loaded with a patient may move from a retracted position (as shown in FIG. 16A) to a first partially extended position (as shown in FIG. 16B and FIG. 16C). The first partially extended position may be a position between the retracted position (as shown in FIG. 16A) and the extended position (as shown in FIG. 16E). In some embodiments, the first partially extended position may be an RT position corresponding to the RT device 330.

After the initial setup, the table top 355 of the couch 350 may be extended to a second partially extended position (as shown in FIG. 16D). The second partially extended position may be a position different from the first partially extended position and between the retracted position (as shown in FIG. 16A) and the extended position (as shown in FIG. 16E). The second partially extended position may be a CT position corresponding to the CT device 320. A treatment CT image may be obtained at the second partially extended position. After the treatment CT image is obtained, the patient may be moved from the CT position of the CT device 320 to the RT position of the RT device 330 for treatment.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the operator's computer, partly on the operator's computer, as a standalone software package, partly on the operator's computer and partly on a remote computer or entirely on the remote computer or server. In the latter scenario, the remote computer may be connected to the operator's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/ or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the descriptions, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method for using in a two-modality apparatus, wherein the two-modality apparatus comprises a couch with a table top, a first modality, and a second modality, the method comprising:
   acquiring an image of a target portion of an object supported on the table top when the table top is at a second working position of the second modality unit;
   determining a second sag of the table top at a second measurement point of the table top according to the image;
   determining a first measurement point of the table top when the table top carrying an object is at a first working position of the first modality unit, wherein the first measurement point of the table top relates to a first isocenter of the first modality unit; and
   estimating, based on the second sag, a first sag of the table top at the first measurement point.

2. The method of claim 1, further comprising:
   causing the two-modality apparatus to move the table top to a vicinity of the first working position of the first modality unit such that a target portion of an object supported on the table top aligns, according to the first sag, with the first isocenter of the first modality unit.

3. The method of claim 1, wherein the second measurement point of the table top relates to a second isocenter of the second modality unit.

4. The method of claim 3, wherein the second isocenter is in a scan plane of the second modality unit and deviates from a scanning center of the second modality unit by a vector in the scan plane.

5. The method of claim 3, wherein the second isocenter includes a scanning center of the second modality unit.

6. The method of claim 1, the estimating, based on the second sag, the first sag of the table top at the first measurement point comprising:
   retrieving standard data that provide a relationship between a sag of the table top and a position of the table top.

7. The method of claim 6, wherein the standard data comprise a plurality of standard data sets, and at least one of the plurality of standard data sets comprises a first standard parameter and a second standard parameter, and wherein:
   the first standard parameter includes a relationship between a sag of the table top and an amount of extension of the table top when the table top is at a working position of the first modality unit, and
   the second standard parameter includes a relationship between a sag of the table top and an amount of extension of the table top when the table top is at a working position of the second modality unit.

8. The method of claim 7, wherein the second standard parameter is determined based on at least one image, wherein the at least one image is acquired at the working position of the first modality unit and with the object carried on the table top.

9. The method of claim 1, wherein the first modality unit is a Linear Accelerator (LINAC) device.

10. The method of claim 1, wherein the second modality unit is a computed tomography (CT) device.

11. A system comprising:
a two-modality apparatus, wherein the two-modality apparatus comprises a couch with a table top, a first modality unit, and a second modality unit;
at least one processor, and
a storage device for storing instructions that, when executed by the at least one processor, cause the system to effectuate operations comprising:
acquiring an image of a target portion of an object supported on the table top when the table top is at a second working position of the second modality unit;
determining a second sag of the table top at a second measurement point of the table top according to the image;
determining a first measurement point of the table top when the table top carrying an object is at a first working position of the first modality unit, wherein the first measurement point of the table top relates to a first isocenter of the first modality unit; and
estimating, based on the second sag, a first sag of the table top at the first measurement point.

12. The system of claim 11, wherein the system is further caused to effectuate the operations comprising:
causing the two-modality apparatus to move the table top to a vicinity of the first working position of the first modality unit such that a target portion of an object supported on the table top aligns, according to the first sag, with the first isocenter of the first modality unit.

13. The system of claim 11, wherein the second measurement point of the table top relates to a second isocenter of the second modality unit.

14. The system of claim 13, wherein the second isocenter is in a scan plane of the second modality unit and deviates from a scanning center of the second modality unit by a vector in the scan plane.

15. The system of claim 13, wherein the second isocenter includes a scanning center of the second modality unit.

16. The system of claim 11, the estimating, based on the second sag, the first sag of the table top at the first measurement point comprising:
retrieving standard data that provide a relationship between a sag of the table top and a position of the table top.

17. The system of claim 16, wherein the standard data comprise a plurality of standard data sets, and at least one of the plurality of standard data sets comprises a first standard parameter and a second standard parameter, and wherein:
the first standard parameter includes a relationship between a sag of the table top and an amount of extension of the table top when the table top is at a working position of the first modality unit, and
the second standard parameter includes a relationship between a sag of the table top and an amount of extension of the table top when the table top is at a working position of the second modality unit.

18. The system of claim 17, wherein the second standard parameter is determined based on at least one image, wherein the at least one image is acquired at the working position of the first modality unit and the object carried on the table top.

19. The system of claim 11, wherein the first modality unit is a Linear Accelerator (LINAC) device and the first modality unit is a Linear Accelerator (LINAC) device.

20. A non-transitory computer readable medium comprising executable instructions that, when executed by at least one processor, cause the at least one processor to effectuate a method for using in a two-modality apparatus, wherein the two-modality apparatus comprises a couch with a table top, the method comprising:
acquiring an image of a target portion of an object supported on the table top when the table top is at a second working position of the second modality unit;
determining a second sag of the table top at a second measurement point of the table top according to the image;
determining a first measurement point of the table top when the table top carrying an object is at a first working position of the first modality unit, wherein the first measurement point of the table top relates to a first isocenter of the first modality unit; and
estimating, based on the second sag, a first sag of the table top at the first measurement point.

* * * * *